United States Patent [19]

Rosenblatt et al.

[11] Patent Number: 5,929,747

[45] Date of Patent: Jul. 27, 1999

[54] BLADDER RETRAINING DEVICES AND METHODS

[75] Inventors: Peter L. Rosenblatt, Chestnut Hill, Mass.; Michael J. Magliochetti, Iowa City, Iowa

[73] Assignee: UroSurge, Inc., Coralville, Iowa

[21] Appl. No.: 08/664,247

[22] Filed: Jun. 7, 1996

Related U.S. Application Data

[63] Continuation-in-part of application No. 08/486,365, Jun. 7, 1995, abandoned.

[51] Int. Cl.[6] .................................................. G08B 1/00
[52] U.S. Cl. .................... 340/309.15; 340/604; 340/573; 340/309.3; 128/886; 604/361; 368/109
[58] Field of Search ............................. 340/604, 309.15, 340/309.3, 573; 128/733, 734, 885, 886; 604/361; 368/107–109

[56] References Cited

U.S. PATENT DOCUMENTS

| | | | |
|---|---|---|---|
| 3,735,101 | 5/1973 | Stewart | 235/92 |
| 4,258,354 | 3/1981 | Carmon et al. | 340/309.4 |
| 4,293,845 | 10/1981 | Villa-Real | 340/309.3 |
| 4,302,752 | 11/1981 | Weitzler | 340/309.1 |
| 4,490,711 | 12/1984 | Johnston | 340/309.4 |
| 4,504,153 | 3/1985 | Schollmeyer et al. | 368/10 |
| 4,801,921 | 1/1989 | Zigenfus | 340/309.15 |
| 4,831,562 | 5/1989 | McIntosh et al. | 340/309.15 |
| 4,853,854 | 8/1989 | Behar et al. | 364/413.01 |
| 4,891,993 | 1/1990 | Barker | 73/863.52 |
| 4,977,906 | 12/1990 | DeScipio | 128/885 |
| 5,074,317 | 12/1991 | Bondell et al. | 128/886 |
| 5,088,056 | 2/1992 | McIntosh et al. | 340/309.15 |
| 5,277,197 | 1/1994 | Church et al. | 128/733 |
| 5,289,157 | 2/1994 | Rudick et al. | 340/573 |
| 5,365,496 | 11/1994 | Tolan-Samilow | 368/109 |
| 5,408,443 | 4/1995 | Weinberger | 340/309.15 |
| 5,416,469 | 5/1995 | Colling | 340/573 |
| 5,423,329 | 6/1995 | Ergas | 128/733 |
| 5,424,719 | 6/1995 | Ravid | 340/573 |
| 5,568,128 | 10/1996 | Nair | 340/604 |

*Primary Examiner*—Jeffery A. Hofsass
*Assistant Examiner*—Ashok Mannava
*Attorney, Agent, or Firm*—Thomas J. Engellenner; Nutter, McClennen & Fish, LLP

[57] ABSTRACT

Devices and methods to simply prompt and record medical events provide improved medical treatment devices and methods. A hand-held electronic device can prompt patients regarding and train patients in a medical event. Physicians or other health care workers can program pre-determined time intervals for scheduled medical events into the device. An alarm can prompt the patients regarding the scheduled medical events at the pre-determined time intervals. Patients can enter scheduled and non-scheduled medical events into the device. The health care workers can access this information from the device directly or the information can be downloaded to an office personal computer for permanent recording in the patient's chart. In another embodiment, the device can determine a compliance rate based upon the occurrence of the medical events. This compliance rate can be compared with a pre-determined target rate. The pre-determined time intervals can be advanced to new intervals when the compliance rate is equal to or greater than the pre-determined target rate; and further advanced if a more rapid retraining rate is desired. In still another embodiment, the device can display informational and/or instructional messages to patients. Switches or other means can allow patients to turn off the alarm during sleep or other standby intervals. Notwithstanding, the patient can still record medical events while the device is in its alarm-standby mode.

20 Claims, 23 Drawing Sheets

BLADDER RETRAINING DEVICES AND METHODS

RELATED APPLICATIONS

This application is a continuation-in-part of the U.S. patent application Ser. No. 08/486,365, filed on Jun. 7, 1995 now abandoned.

BACKGROUND OF THE INVENTION

The field of the present invention is medical treatment and, in particular, devices and methods for prompting and recording medical events as in the treatment of urinary incontinence.

It is estimated that 10% of the population of the United States suffer from some degree of urinary incontinence. The two most common causes of urinary incontinence, genuine stress incontinence (GSI) and detrusor instability (DI), make up over 90% of the cases of urinary incontinence. Bladder retraining drills (BRD) are one of the non-surgical treatment methods for urinary incontinence. BRD are based on the assumption that conscious efforts to suppress sensory stimuli will reestablish cortical control of an uninhibited bladder. The technique of BRD involves increasing the capacity of the bladder by gradually prolonging the intervals between voiding. Patients with urinary incontinence (either GSI or DI) tend to void frequently in an effort to keep their bladders from becoming full, which they feel will decrease the quantity of leakage during episodes of incontinence. These patients, however, tend to develop an increased sense of urgency at smaller bladder volumes. By gradually increasing voiding intervals and therefore bladder capacity, a majority of patients with urge incontinence will have either significant improvement or report complete cure of their symptoms.

BRD requires that the patient clearly understand the methods recommended to accomplish BRD to accurately record their progress. Close supervision by health care personnel is essential. A common problem encountered by physicians who prescribe this treatment is patient confusion with the directions for BRD and forgetfulness with the prescribed timing for and recording of voiding.

Portable electronic medical event reminder and monitoring devices have been used to prompt and record events involved in medical treatment. E.g., U.S. Pat. No. 4,504,153 by Schollmeyer et al.; U.S. Pat. No. 4,490,71 1 by Johnston; and U.S. Pat. No. 4,293,845 by Villa-Real. Notwithstanding, the prior art does not allow a patient to input an event, such as a urinary leakage, which falls outside of the pre-determined schedule. In addition, the prior art does not disclose apparatus and methods for changing the pre-determined schedule based on a patient's progress to date to train the patient to reach a desired target.

Accordingly, there is a need for simple devices and methods to prompt a patient of scheduled medical events, and to record both scheduled and non-scheduled medical events. In addition, there is a need for simple devices and methods for changing the pre-determined schedule for a medical event based on a patient's progress to date to train the patient to reach a desired target.

SUMMARY OF THE INVENTION

The present invention discloses simple devices and methods to assist the patient and physician in medical treatment and, in particular, in BRD. It is based on the recognition that simple methods and devices which prompt patients of scheduled medical events and allow patients to record both scheduled and non-scheduled medical events assist the patients in medical event retraining and the physicians in accurately monitoring the patients' progress.

In one embodiment, a hand-held electronic device can prompt patients of and train patients in a medical event. Physicians or other health care workers can program pre-determined time intervals for the scheduled medical events into the device. Alternatively, the health care workers can program the desired settings into an auxiliary programming device, which can then load the pre-determined settings into the patient's hand-held device. An audible, visual or preferably, silent vibrating alarm can prompt the patients of the scheduled medical events at the pre-determined time intervals. Such prompting can occur for a pre-determined duration either once or repeatedly at additional pre-determined intervals until the patient turns off the alarm (or stops the vibration). Alternatively, the device can stop the alarm (or vibration) after a pre-determined duration. Patients can enter scheduled (including medical events at and/or within a selected time period of the scheduled intervals) and non-scheduled medical events into the device. The health care workers can access this information from the device directly via visual displays; or the information can be printed onto a hard-copy data card or other type of print out, and/or downloaded to an office personal computer for permanent recording in the patient's chart.

In other embodiments, the device can determine and display a compliance rate based upon the occurrence of medical events. A rating means can compare this compliance rate with a pre-determined target rate. The pre-determined time intervals can be automatically advanced to new intervals when the compliance rate is equal to or greater than the pre-determined target rate; and can be further advanced to new intervals when the physician and/or patient select a more rapid retraining option by depressing an option selection element.

In still other embodiments, the device can display informational and/or instructional messages to patients. Examples of such messages include the time remaining until the next scheduled medical event, a reminder to turn off the alarm, and a confirmation of the occurrence of a scheduled or non-scheduled medical event. Other messages can include prompts for complementary medical retraining activities, such as, for example, patient exercises. Switches or other means can allow patients to turn off the alarm during sleep or other standby intervals. Notwithstanding, the patient can still record medical events while the device is in its alarm-standby mode. The device can also be capable of activation only upon the entering of an activation code.

Because of such simplicity, the invention reduces patient confusion and allows health care workers to monitor the patients' progress and train patients in a medical event. The present invention is therefore a valuable addition to the art of portable electronic medical event reminder and monitoring devices.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION OF THE INVENTION

The devices and methods of the present invention involve a hand-held electronic instrument which can prompt patients regarding, and train patients with respect to, a medical event. Physicians or other health workers can preprogram the device with pre-determined time intervals for scheduled medical events and a pre-determined target rate. Patients can record their progress with the device. The pre-determined time intervals can be automatically adjusted based upon a comparison between the patients' progress and target rates. Subsequently, clinicians can access records regarding patients' progress directly from the device or download information stored on the device to a remote computer. Although the invention is described with respect to the medical event of urination, it is understood that the invention is applicable to other medical events as well.

Figure 1:
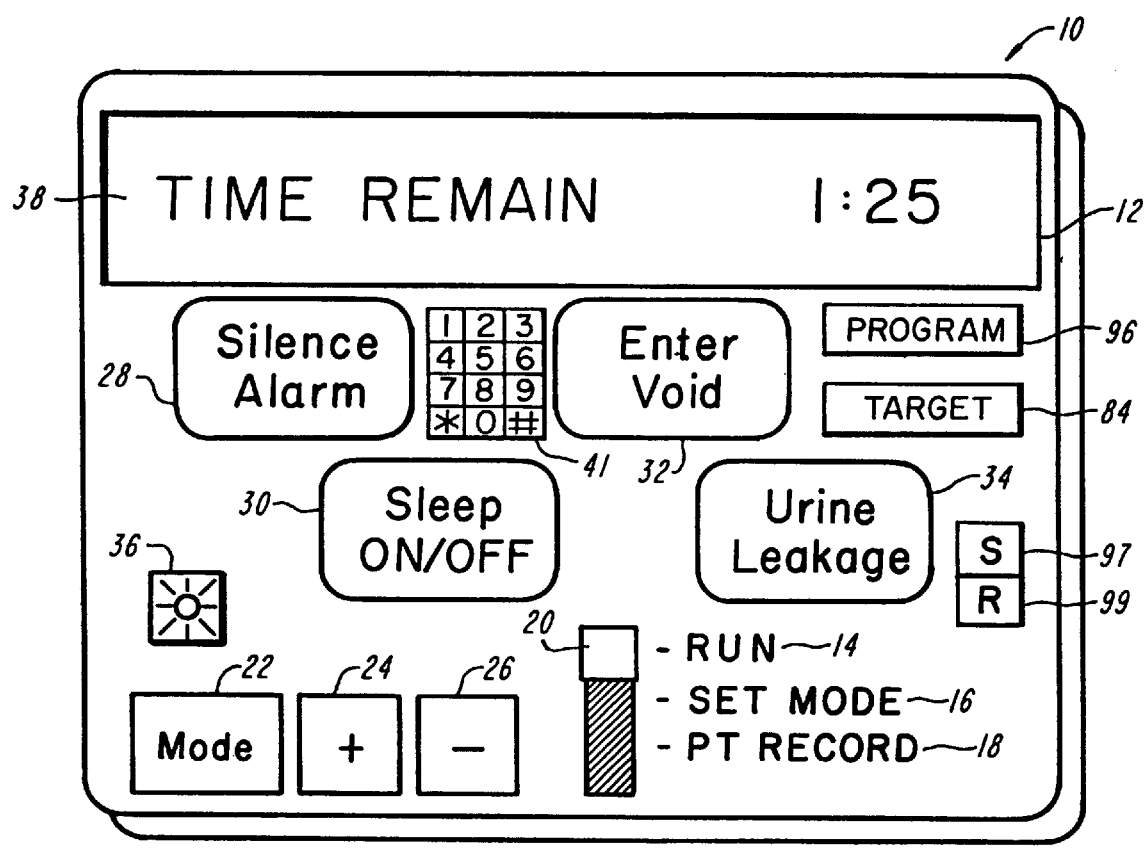
FIG. 1 illustrates the device of the present invention displaying a "TIME REMAIN" message for instructing the patient as to the length of time remaining until the next scheduled medical event.

FIG. 1 illustrates a device 10 which can have an liquid crystal display (LCD) 12 that can show patient messages when the switch 20 is in the "RUN" position 14 to prompt and train patients in urination or voiding according to a pre-determined schedule. For example, a "TIME REMAIN 1:25" message 38 can show the hours and minutes remaining until the next voiding is scheduled.

Figure 2:
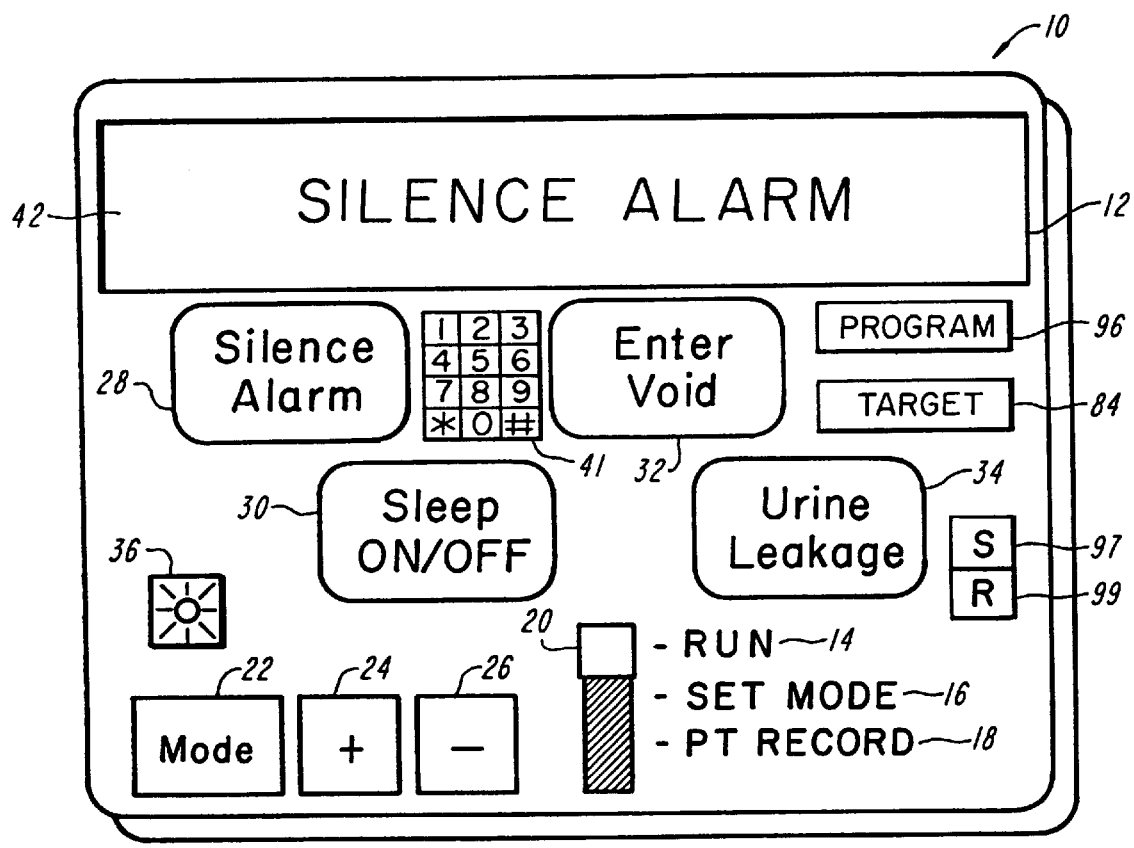
FIG. 2 illustrates the device of the present invention displaying a "SILENCE ALARM" message for instructing the patient that he or she can shut off the alarm because the scheduled time interval has been reached for the next scheduled medical event.

FIG. 2 illustrates a "SILENCE ALARM" message 42, which can blink when an alarm 36 sounds and can instruct the patient that the proper time interval has been reached for the next scheduled voiding. Alternatively, the alarm 36 can cause the device 10 to vibrate to prompt the patient to void. Such prompting can occur for a pre-determined duration either once or at pre-determined intervals until the patient turns off the alarm 36 (or stops the vibration) by pressing a "Silence Alarm" button 28. Alternatively, the device 10 can turn off the alarm 36 or vibration after a pre-determined duration.

Figure 3A:
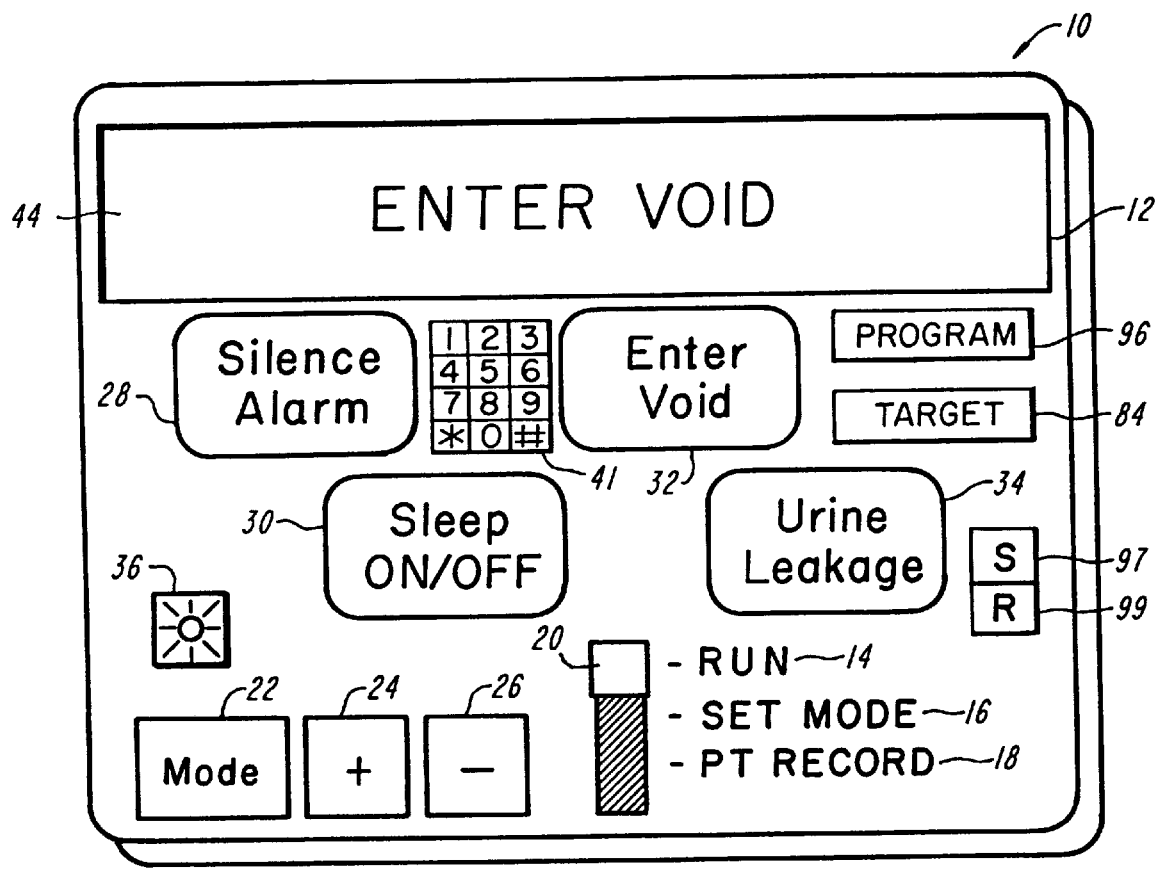
FIG. 3A illustrates the device of the present invention displaying an "ENTER VOID" message for instructing the patient that he or she may enter the time of the medical event, i.e., the voiding.

FIG. 3A illustrates that an "ENTER VOID" message 44 can appear (and can blink) when the patient presses the "Silence Alarm" button 28. The message prompts the patient to enter the time and date of their voiding episode by pressing the "Enter Void" button 32. Pressing of the "Enter Void" button 32 can also reset the interval timer. A "VOID RECORDED" message can be displayed when the patient presses the "Enter Void" button 32 to confirm the entering of a scheduled medical event.

Figure 3B:
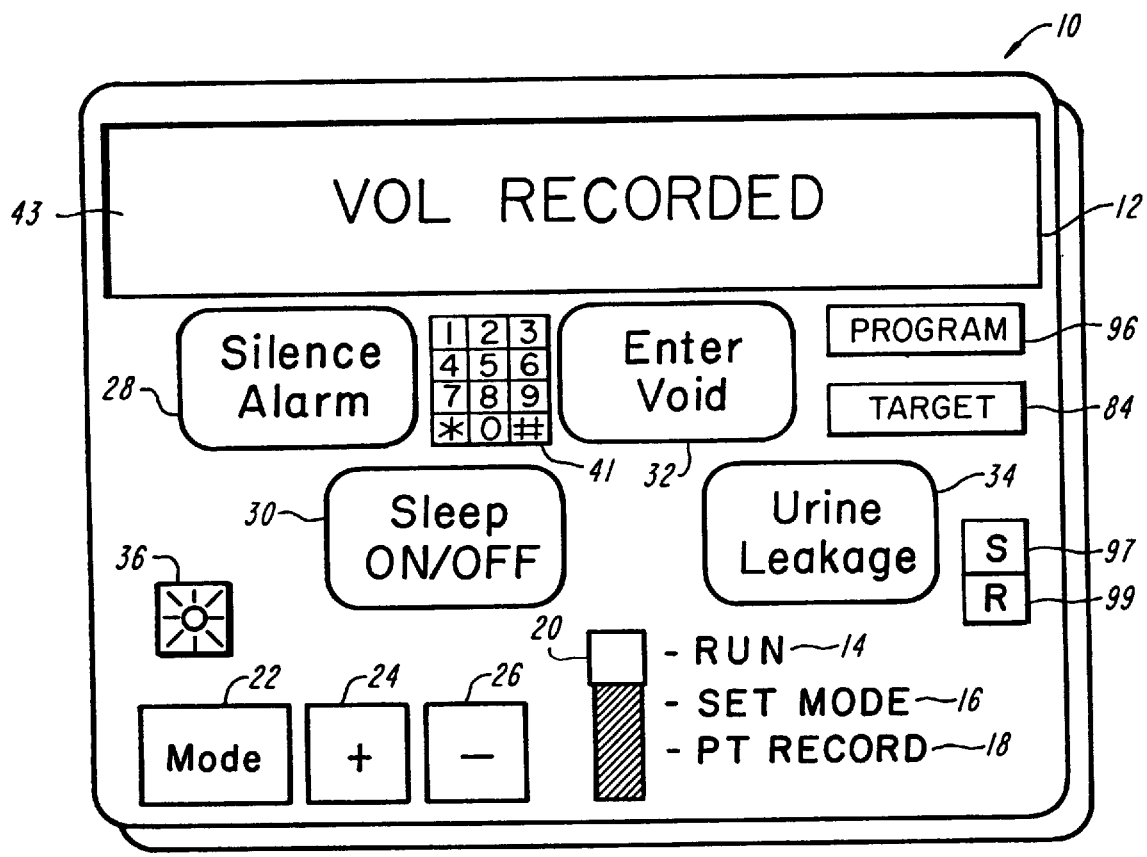
FIG. 3B illustrates the device of the present invention displaying a "VOL RECORDED" message for confirming that a patient has entered the actual volume of a scheduled voiding.

The "ENTER VOID" message 44 can also prompt the patient to enter the actual volume voided, after the patient has measured the actual volume in a urine collection device. FIG. 3B illustrates that a "VOL RECORDED" message 43 can be displayed after the patient has entered the actual volume voided via a number pad 41, or other type of inputting element. For example, the "Enter Void" button 32 (or other buttons of the device 10) can be having an auto-repeat capability such that when the button is held down by the patient, the device 10 can automatically display a sequence of pre-determined values. The patient can then release button 32 when the appropriate value is displayed. The patient can then press the "Enter Void" button 32 again to confirm the entering of the date and time of the scheduled voiding episode and to reset the interval timer.

The device 10 can also be capable of recording a voiding episode which occurs within a selected time period of the scheduled inter-void interval. Thus, a patient who voids within, for example, 15 minutes of a scheduled 3 hour inter-void interval, can still record the date, time and/or volume of the voiding episode by pressing the "Enter Void" button 32 and reset the interval timer.

Figure 4:
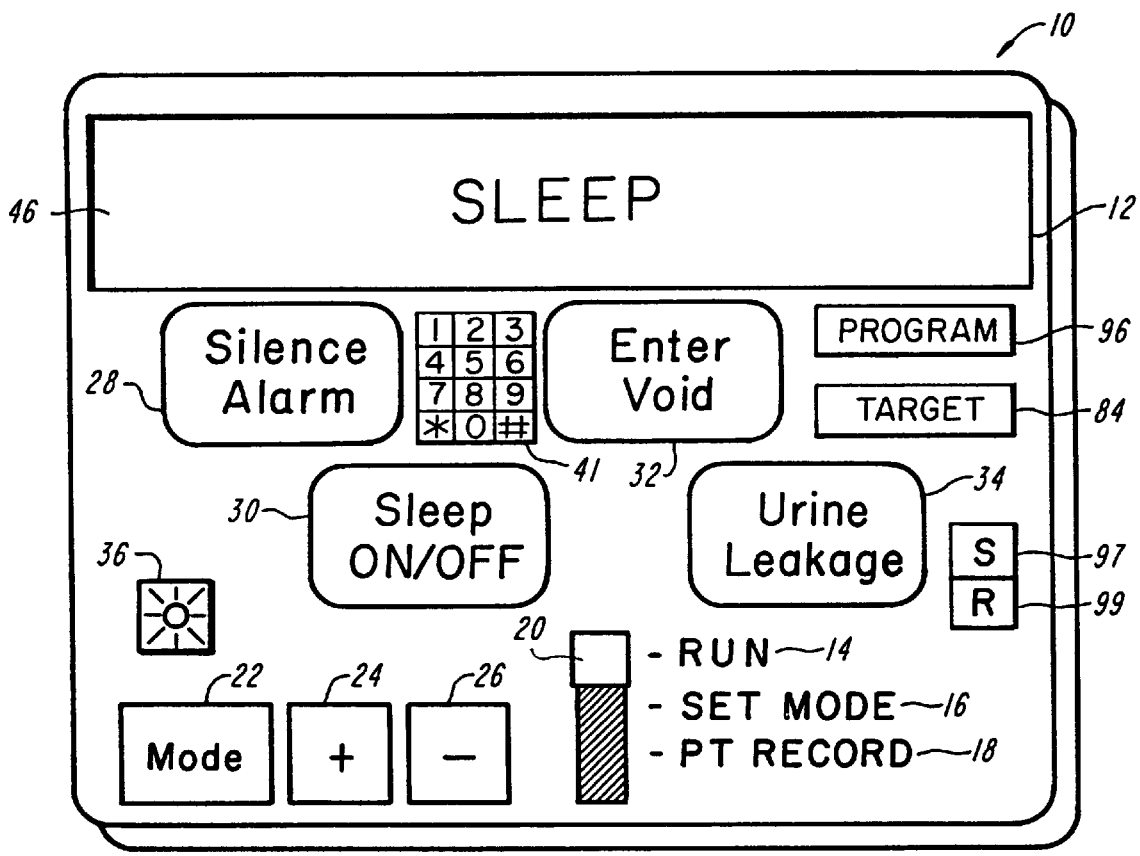
FIG. 4 illustrates the device of the present invention displaying a "SLEEP" message for instructing the patient that the device is in standby state during which the alarm will not prompt the patient.

FIG. 4 illustrates that a "SLEEP" message 46 can appear when patients press a "Sleep ON/OFF" button 30, as shown in FIG. 4. By pressing the "SLEEP ON/OFF" button 30, the patient can keep the device in a standby state so that he or she will not be disturbed by the alarm 36 at night. While the patient is sleeping, the interval timer can continue to run, however, until the end of the pre-determined inter-void time interval is reached. By pressing the "Sleep ON/OFF" button 30 again, the patient can end the standby state and can restart the interval timer with the alarm 36. The device 10 can be also pre-programmed with a maximum sleep duration (e.g., 9 hours) such that the device 10 will terminate the standby state and restart the interval timer with the alarm 36 after such a duration. Patients can still enter the date and time of voids at night (the number of which can also be recorded as a "nocturia" value for the clinicians) by pressing the "Enter Void" button 32, but this will not activate the interval timer with the alarm 36. Patients can also enter the volume of the nighttime voiding episodes via the number pad 41, and the device can confirm the volume entries by displaying the "VOL RECORDED" message 43, as described above in the context of FIG. 3B.

The device 10 can be adapted to distinguish voiding episodes entered within a selected time period of the patient pressing the "SLEEP ON/OFF" button 30 from other types of voiding and/or leak episodes. Accordingly, the voiding episodes of a patient who is purposely attempting to void prior to going to sleep for the night, in accordance with a physician's instructions, can be distinguished from the other results of the patient's progress.

In the event that a patient takes a nap, the patient can also press the "SLEEP ON/OFF" button 30 to silence the alarm 36. When the patient awakes and again presses the button 30, the interval timer will continue to run if the end of the pre-determined time interval has not been reached. Thus, the inter-void interval will not be lengthened solely because of a nap, unless the patient naps longer than the time remaining before the next scheduled medical event prompt.

Figure 5:
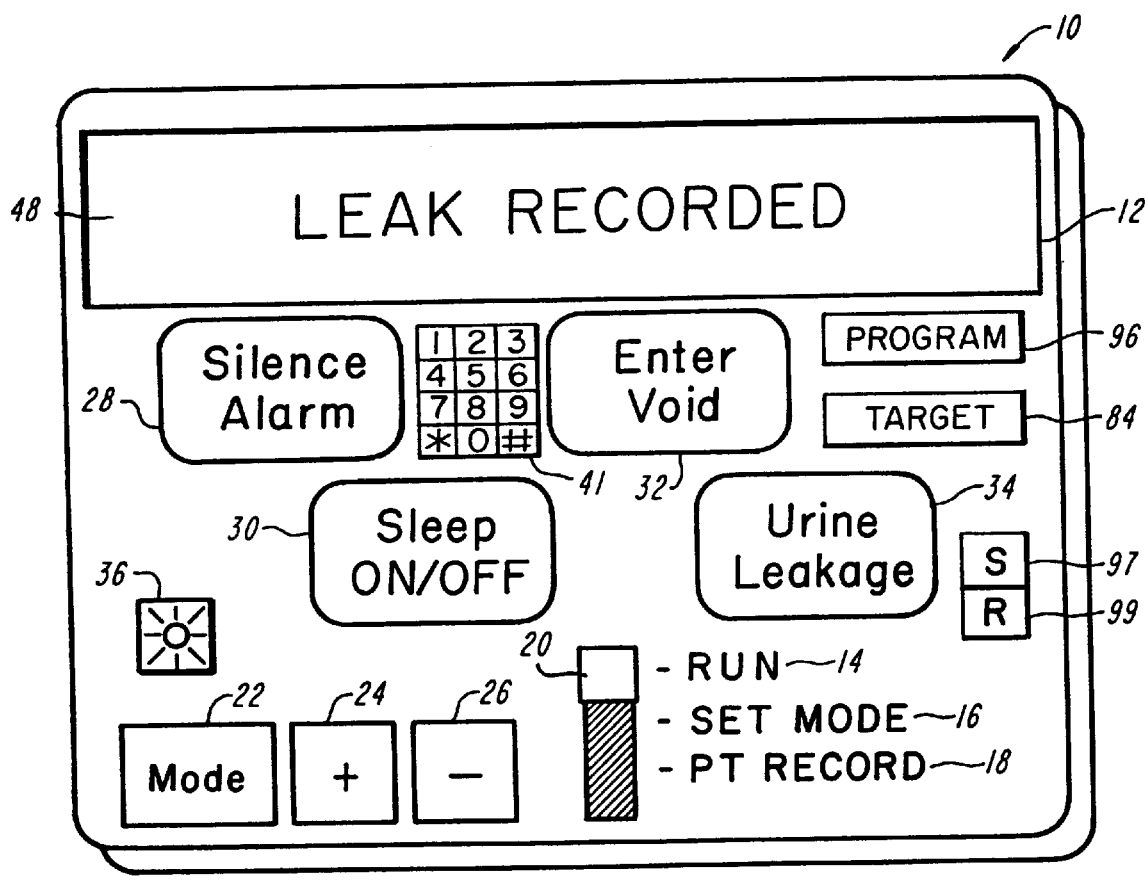
FIG. 5 illustrates the device of the present invention displaying a "LEAK RECORDED" message for confirming to the patient that he or she has entered an unscheduled medical event, e.g., a urinary leakage.

FIG. 5 illustrates that a "LEAK RECORDED" message 48, analogous to the "VOID RECORDED" message discussed above, can appear for a brief period of time, such as about 5 seconds, when the "Urine Leakage" button 34 is pressed by patients for recording the date and time of episodes of urinary incontinence. Patients can also enter the volume of the leaking episode via the number pad 41, or employ another type of inputting device, such as a button 34 having auto-repeat capability, as discussed above in the context of button 32. The device 10 can then confirm the volume entries by displaying the "VOL RECORDED" message 43, as illustrated previously in FIG. 3B. In an alternative embodiment, when a patient has not had the time to collect and/or measure the volume associated with a leak episode, the patient can enter a value, such as, for example, 1, 2 or 3, to indicate the severity of a leak episode.

Figure 6:
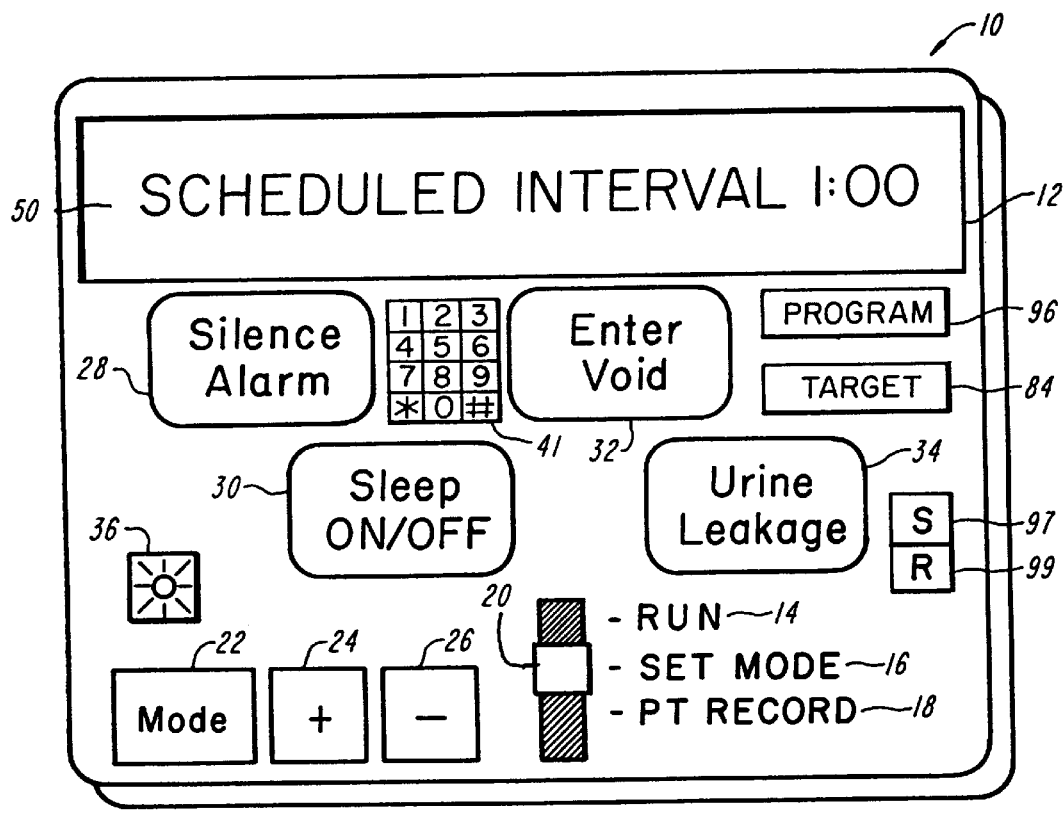
FIG. 6 illustrates the device of the present invention displaying an "SCHEDULED INTERVAL 1:00" message which indicates the scheduled time interval between medical events.

A clinician can preset the intervals between scheduled voidings by moving the switch 20 from the "RUN" position 14 to the "SET MODE" position 16, as shown in FIG. 6. In an alternative embodiment, the device 10 can be equipped without the mode buttons "RUN" 14, "SET MODE" 16, and PT RECORD" 18, and the different modes of the device can be changed by pressing various buttons on the device in a pre-determined sequence. The LCD 12 can display a "SCHEDULED INTERVAL 1:00" message 50 as a default value for the scheduled voiding interval. The clinician can use the "+" button 24 and the "−" button 26, or use another type of increasing/decreasing mechanism, such as other buttons of the device 10 having auto-repeat capabilities, to increase or decrease this time to the desired inter-void interval. For example, the clinician can change the initial time interval to one hour and thirty minutes. Accordingly, the LCD 12 will show a "SCHEDULED INTERVAL 1:30" message 50 and the patient will be scheduled to void every hour and 30 minutes.

Figure 7:
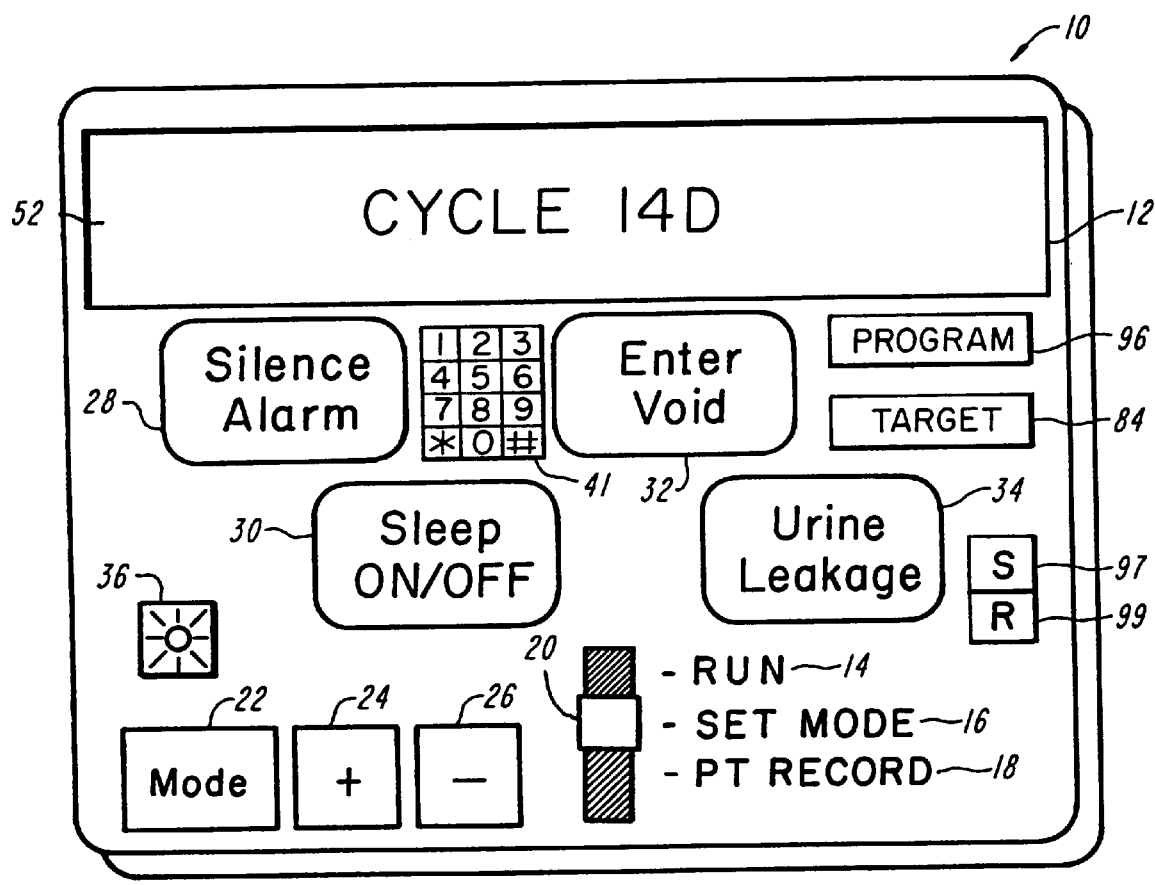
FIG. 7 illustrates the device of the present invention displaying a "CYCLE 14D" message which indicates a 14 day treatment cycle.

FIG. 7 illustrates that the clinician can press the Mode button 22, or employ other types of mode changing mechanisms, and a new "CYCLE 14 D" message 52 can appear as a default value for the cycle or the interval of time before the scheduled voiding interval 50 is automatically adjusted. The clinician can use the "+" button 24 and "−" button 26 or use another type of increasing/decreasing mechanism, to adjust this number of days. For example, the clinician can adjust this cycle setting to ten days. Accordingly, the LCD 12 will show a "CYCLE 10 D" message 52 and the device 10 will automatically adjust the length of time between scheduled voidings after 10 days.

Figure 8:
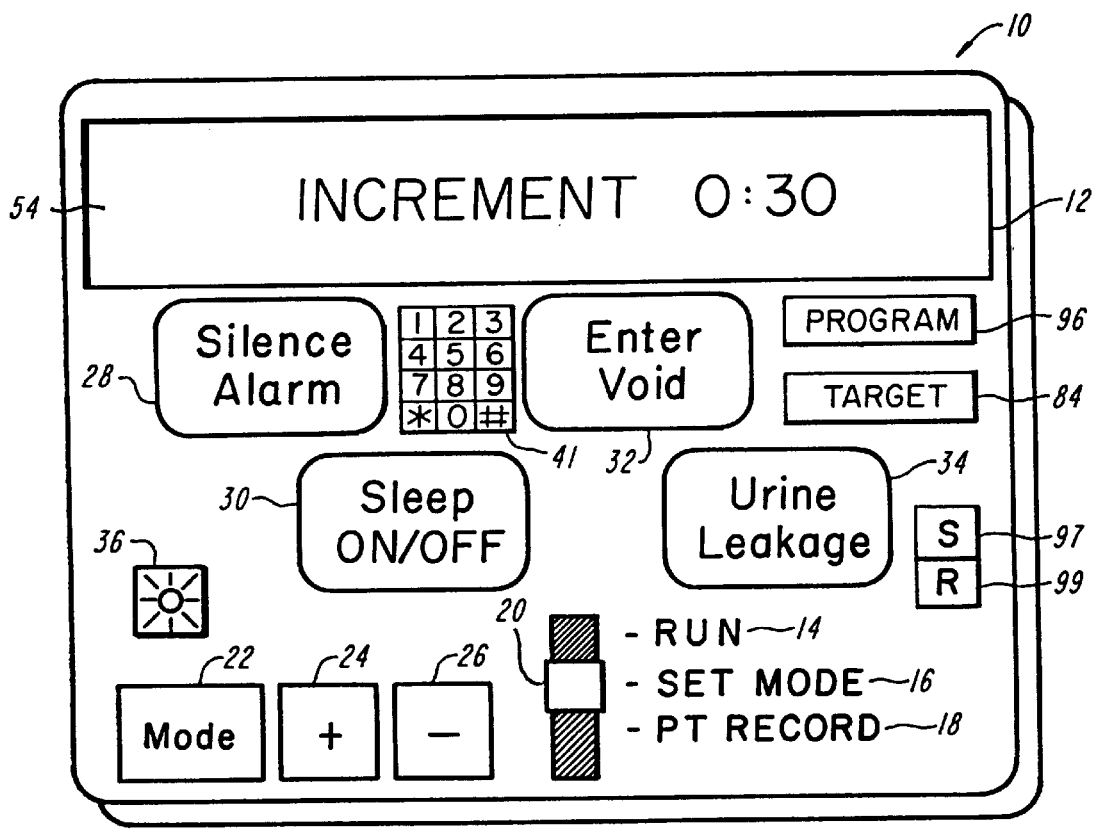
FIG. 8 illustrates the device of the present invention displaying an "INCREMENT 0:30" message which indicates the increment of time to be added to the scheduled time interval between medical events.

FIG. 8 shows that the clinician can press the Mode button 22 again, or employ other types of mode changing mechanisms, and a new "INCREMENT 0:30" message 54 can appear as a default value for the increment of time to be added to the scheduled interval between voidings. The clinician can use the "+" button 24 and "−" button 26 or use another type of increasing/decreasing mechanism, to adjust this increment of time. For example, the clinician can change this increment to fifteen minutes. Accordingly, the LCD 12 will show an "INCREMENT 0:15" message 54 and the device 10 will increase the length of time between scheduled voidings to one hour and 45 minutes.

Figure 9:
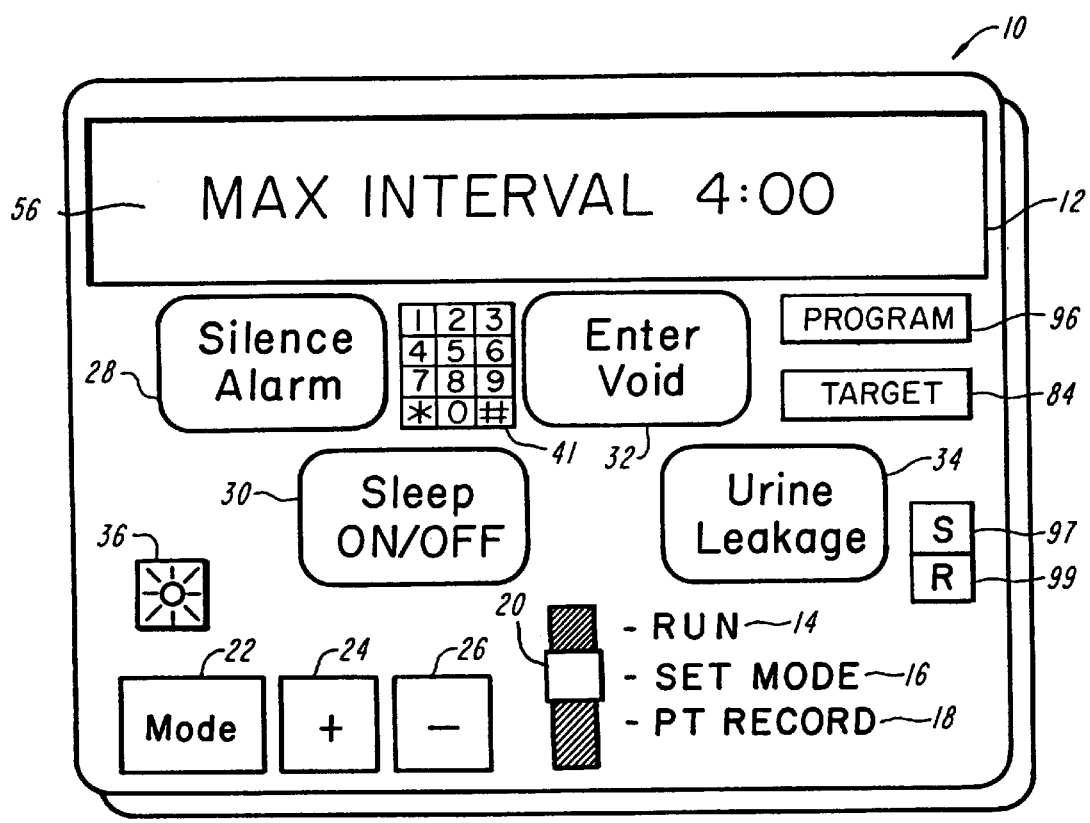
FIG. 9 illustrates the device of the present invention displaying the maximum scheduled time interval, i.e., 4 hours, between medical events.

FIG. 9 illustrates that the clinician can press the Mode button 22 or employ other types of mode changing mechanisms, again, and a new "MAX INTERVAL 4:00" message 56 can appear as a default value for the maximum scheduled interval between voidings. The clinician can use the "+" button 24 and the "−" button 26 or use another type of increasing/decreasing mechanism, to adjust this maximum interval. For example, the clinician can change this maximum interval to four hours and the display can show a "MAX INTERVAL 3:00" message 56.

Thus, in the examples above, if the "SCHEDULED INTERVAL" is set at "1:30", the "CYCLE" is set at "10 D", and the "INCREMENT" is set at "0:15", then after ten days, the interval will change from "1:30" to "1:45". After another ten days, the interval will increase to "2:00". This will continue until the interval reaches "3:00", after which the interval will no longer change.

Clinical personnel can also set the actual date and time while the switch 20 is in the "SET MODE" position 16. By repeatedly pressing the Mode button 22, a "SET MONTH 01" message; a "SET DAY 01" message; a "SET YEAR 1995" message; a "SET HOUR 12:00 AM" message; a "SET MIN 12:00 AM" message; and a "SET 12:00 AM" message, can appear consecutively as default values. At each month, day, year, hour, minute and AM/PM default value, one can then use the "+" button 24 "−" button 26 to set the actual date and time. Alternatively, clinicians can employ other types of mode changing mechanisms and/or other types of increasing/decreasing mechanisms, known those of ordinary skill in the art of electronic reminder and monitoring devices, to set the date and time of the clock portion of the device.

In another embodiment of the device 10, the health care workers can program the desired settings into an auxiliary programming device. The desired setting can then be loaded into the patient's hand-held device by interfacing the auxiliary device with the patient's hand-held device. Such an arrangement permits an even more compact (i.e., pager-size) hand-held device for the patient.

Figure 10A:
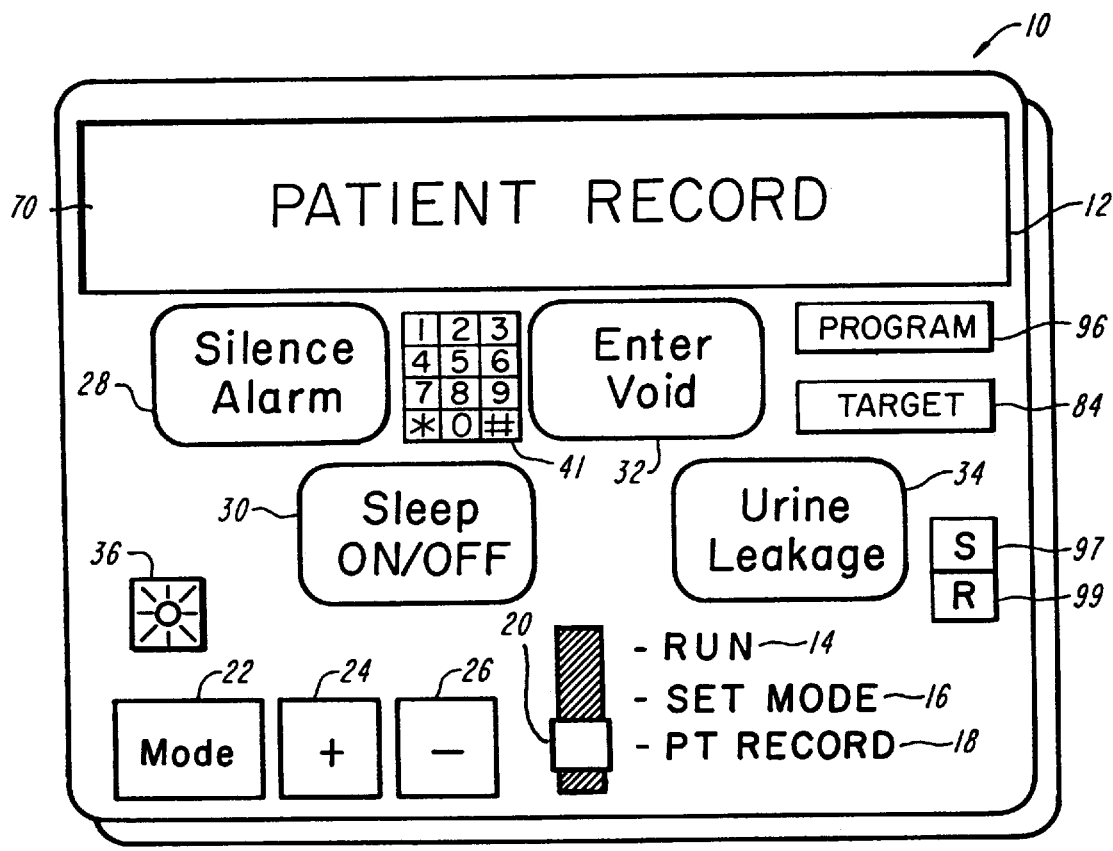
FIG. 10A illustrates the device of the present invention displaying a "PATIENT RECORD" message for showing the physician that he or she can retrieve the patient records from the device.

A clinician can retrieve a record of a patient's progress by moving the switch 20 to a "PATIENT RECORD" position 18 and adjusting the values with the Mode button 22 as well as the "+" button 24 and "−" button 26. Alternatively, clinicians can employ other types of mode changing mechanisms and/or other types of increasing/decreasing mechanisms known to those of ordinary skill in the art of electronic reminder and monitoring devices, as discussed above, to retrieve patient records. Once the switch 20 is moved to the "PATIENT RECORD" position 18, the LCD 12 can display a "PATIENT RECORD" message 70, as shown in FIG. 10A.

Figure 10B:
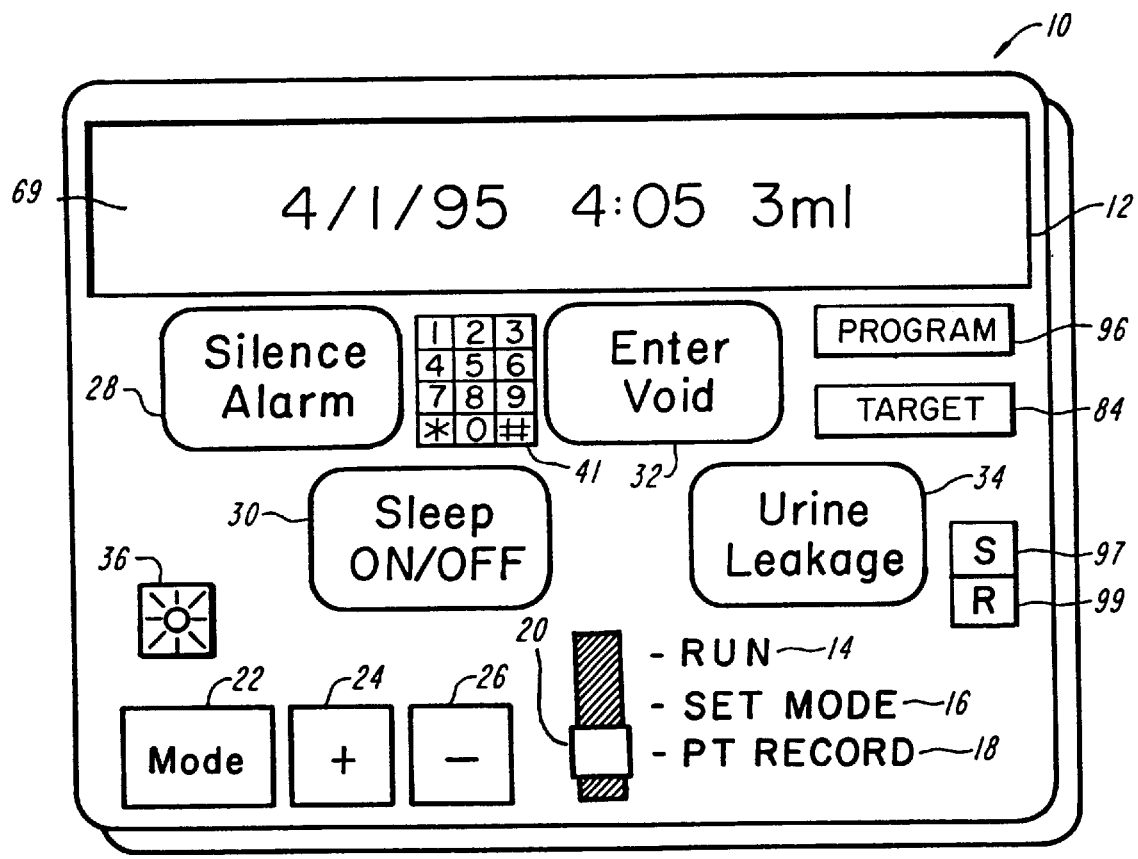
FIG. 10B illustrates the device of the present invention displaying a sequential chronicle of the date, time and/or volume of the scheduled and unscheduled voiding episodes recorded by the patient.

The record of the patient's progress can be displayed in a variety of ways, by repeatedly pressing the "+" button 24. For example, the clinician can retrieve a sequential chronicle 69 of the date, time and/or volume of the scheduled and unscheduled voiding episodes recorded by the patient over a pre-determined time period (e.g., per one week), as illustrated in FIG. 10B. Other ways of displaying a patient's progress to date include, but are not limited to, a display of date and "VOIDING FREQUENCY" based upon the number of scheduled and unscheduled voiding episodes recorded by the patient over a pre-determined time period (e.g., per one 24-hour period); a display of "AVERAGE VOIDING FREQUENCY" and/or "AVERAGE VOIDING VOLUME" based upon the average number of scheduled and unscheduled voids and associated average voiding volumes recorded by the patient over a pre-determined time period (e.g., per one week); and/or a display of a "VOIDING FREQUENCY RANGE" based upon the minimum and maximum Voiding Frequencies during a first pre-determined time period (e.g., per one 24-hour period), compared over a second pre-determined time period (e.g., per one week).

Figure 11:
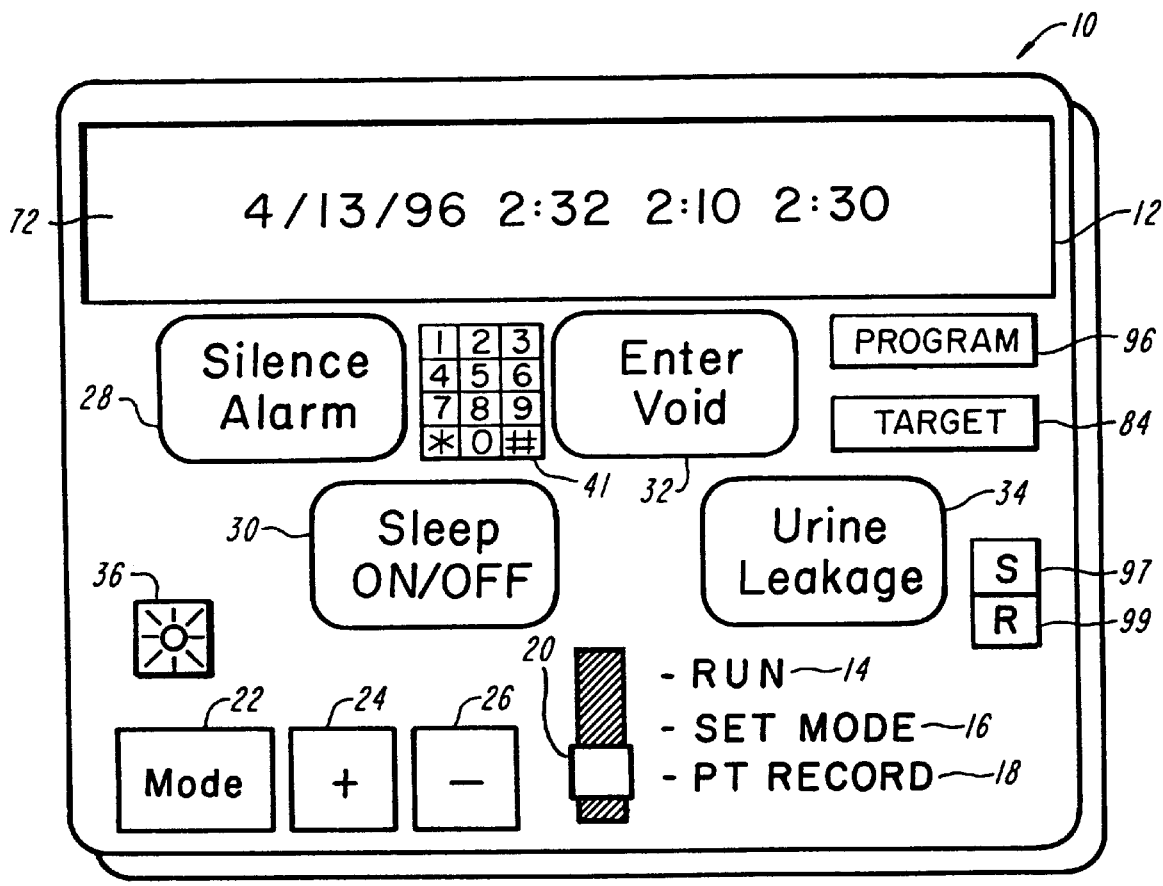
FIG. 11 illustrates the device of the present invention displaying a display of the actual intervals between the medical events entered by a patient.

The clinician can also retrieve a sequential display of the date and time of actual intervals 72 between patient voids, as shown in FIG. 11. Alternatively, the clinician can retrieve an average inter-void interval rate ("AVERAGE IVI RATE") based upon the average inter-void interval over a pre-determined time period (e.g., per one week); and/or an inter-void interval range ("IVI RANGE") based upon the minimum and maximum IVI Rate during a first pre-determined time period (e.g., per one 24-hour period), compared over a second pre-determined time period (e.g., per one week).

The clinician can further retrieve a "SCHEDULED VOID RATE" based on the number of voidings at the scheduled time intervals over a pre-determined time period (e.g., per one week).

Figure 12:
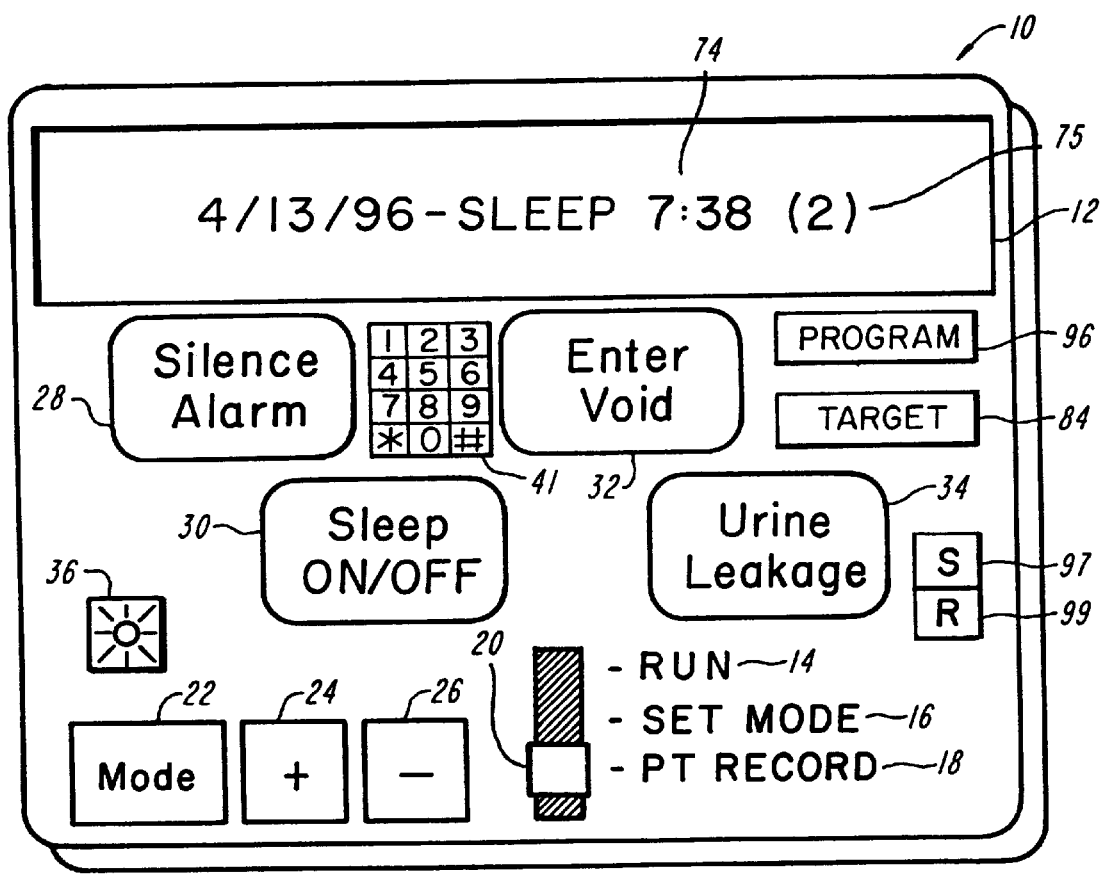
FIG. 12 illustrates the device of the present invention displaying the duration of a sleep period entered by a patient.

In addition, the clinician can retrieve a display of the nocturia values 75 (number of nighttime voiding episodes) and duration of associated "sleep" periods 74, as shown in FIG. 12 Alternatively, the clinician can retrieve a chronicle of the date, time and volume of nighttime voiding episodes; an "AVERAGE NOCTURIA RATE" and an "AVERAGE SLEEP RATE" based upon, respectively, the average number of nighttime voids and the average duration of associated sleep periods entered while the device was in a standby state over a pre-determined time period (e.g., per one week); and/or a "NOCTURIA RATE RANGE" and "SLEEP PERIOD RANGE" indicating, respectively, the minimum and maximum nocturia values and sleep periods compared over a pre-determined time period range (e.g., per one week). The LCD can display the "PATIENT RECORD" message 70 to show when the last recorded interval has been displayed.

A clinician can retrieve patient record entries in reverse order on the LCD 12 by repeatedly pressing the "−" button 26 when the "PATIENT RECORD" message 70 is displayed. After the very first entry is displayed, the LCD 12 can show the "PATIENT RECORD" message 12 again.

A clinician can return to the "PATIENT RECORD" message 70 (i.e. the beginning of the record) on the LCD 12 pressing the "+" button 24 and the "−" button 26 simultaneously at any time during the patient record retrieval process.

Figure 13:
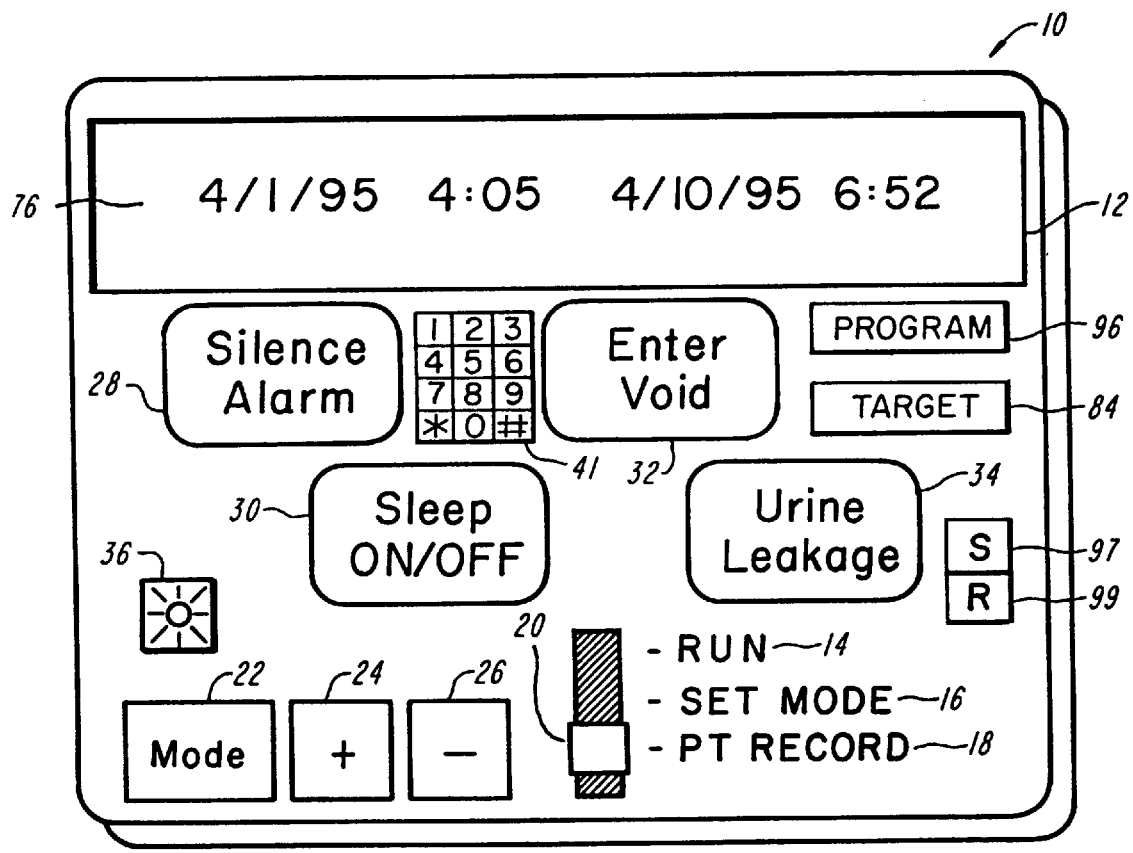
FIG. 13 illustrates the device of the present invention displaying a chronicle of the non-scheduled medical events by date and time entered by a patient.

A clinician can retrieve a chronicle 76 of the date, time and/or volume of leaking episodes recorded by the patient on the LCD 12, as shown in FIG. 13, by pressing the Mode button 22. Alternatively, the clinician can retrieve a "AVERAGE LEAK RATE" based upon the average number of leaking episodes over a pre-determined time period (e.g., per one week); and/or a "LEAK RATE RANGE" indicating the minimum and maximum number of leaking episodes occurring during a first pre-determined time period (e.g., per one night), compared over a pre-determined time period range (e.g., per one week).

Thus, the ability of clinicians to access results such as, for example, inter-void intervals, voiding, nocturia, and leaking episode frequency and/or volumes with actual time and date of events, if so desired, can be beneficial for determining the times of day and/or week when the patient has the most severe symptoms, and can assist, for example, in determining dosing schedules for anticholinergic drugs.

Figure 14:
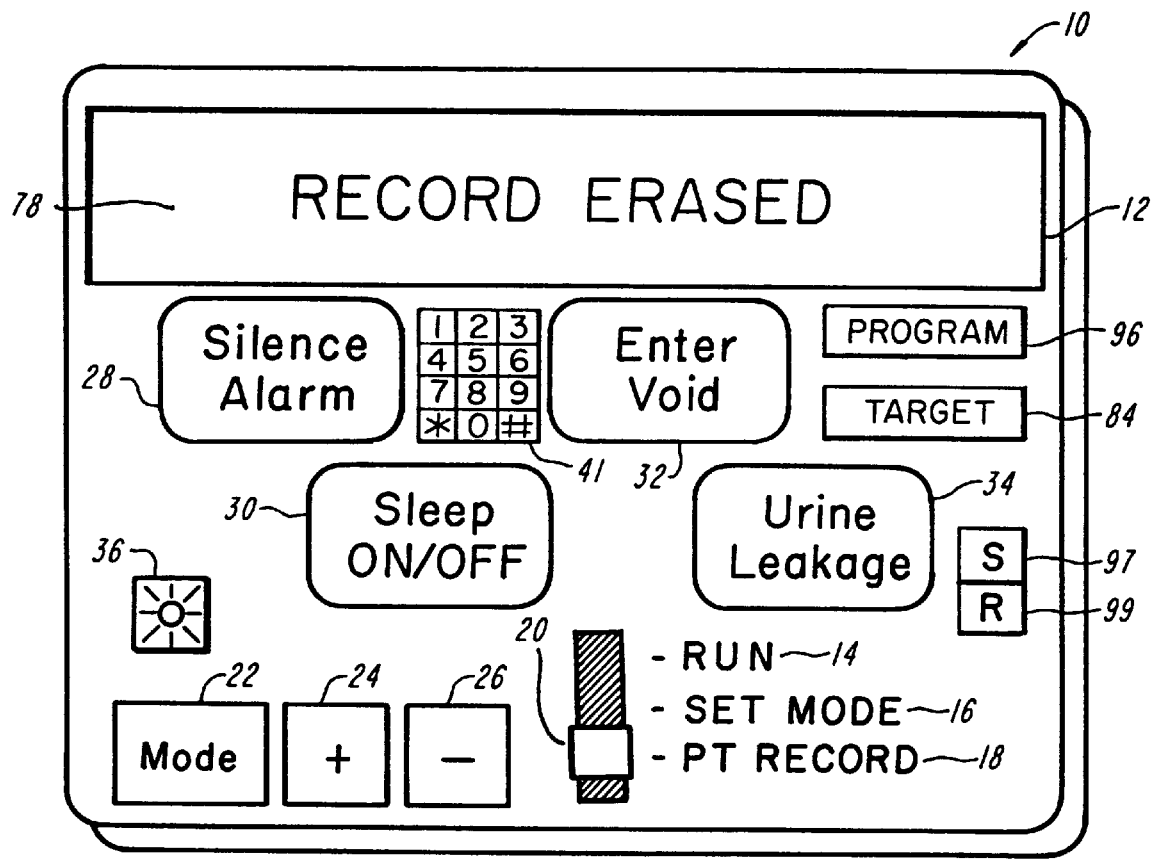
FIG. 14 illustrates the device of the present invention displaying a "RECORD ERASED" message which indicates that the previous patient's record has been erased.

A clinician can erase the current patient record by simultaneously pressing the "Silence Alarm" button 28 and "Sleep ON/OFF" button 30 while the switch 20 is set to the "PATIENT RECORD" position 18. The LCD 12 can then display the "RECORD ERASED" message 78, as illustrated in FIG. 14.

A clinician can place the switch in the "RUN" position to reset the device for patient prompting and training.

Figure 15A:
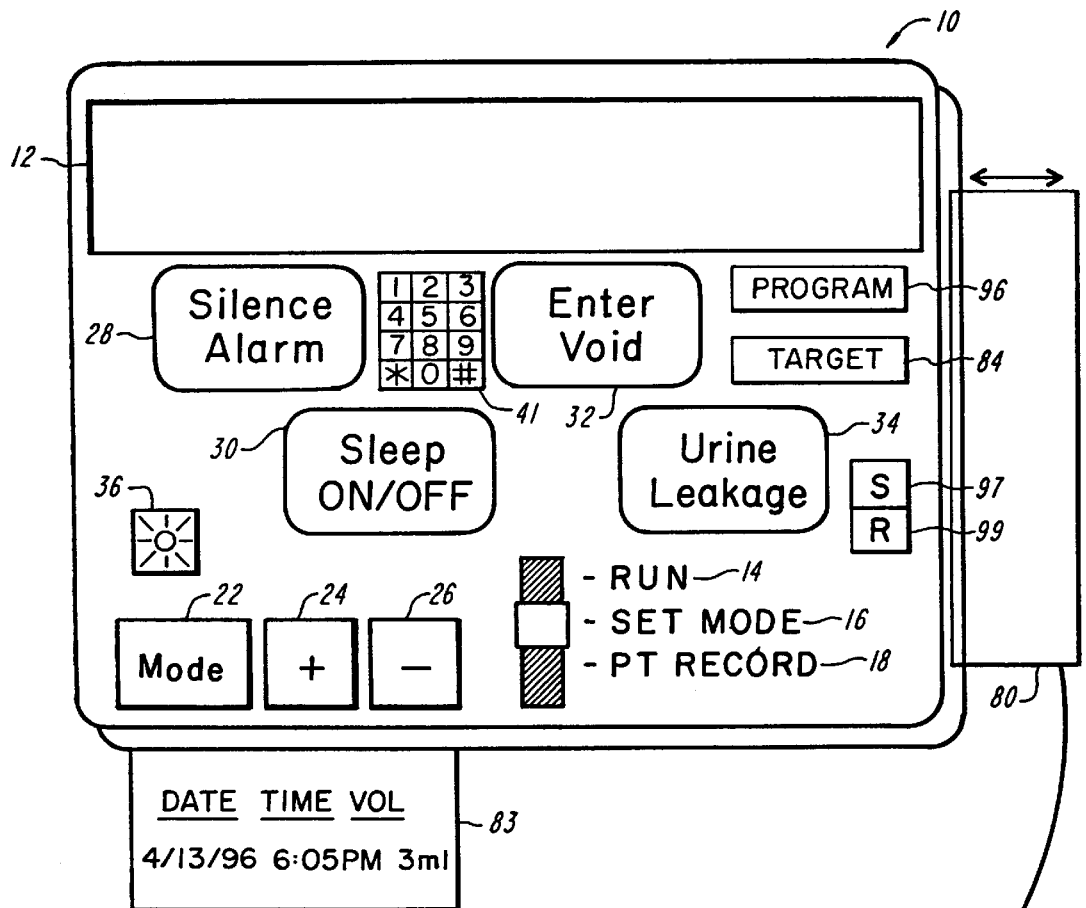
FIG. 15A the device of the present invention having the capacity to store the record of the patient on disk and/or on a hard copy data card.
Figure 15B:
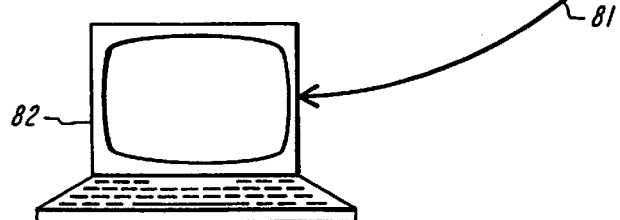
FIG. 15B illustrates the device of the present invention having the capacity to transmit the preset parameters and the patient's record by modem to the physician's computer.

The device can also have the ability to download the patient record on a personal computer, so that a hard copy of the patients' record, including the pre-set parameters and results, can be printed out and placed in the patients' chart to monitor progress with bladder retraining. For example, the device 10 can have the capacity to store the records on a disk 80, as shown in FIG. 15A. This disk 80 can then be removed and inserted into a remote computer 82 for record retrieval, as shown in FIG. 15B. Alternatively, the device 10 can have the ability to transmit the patient's record by modem 81 to a remote computer 82 at, for example, a regional health center, and the clinician can then interpret the results and input changes back to the device 10 via the modem. In still another embodiment, the device 10 can have the ability to print out results onto a hard copy data card 83, as illustrated in FIG. 15A, which can be removed for review by the clinician and directly inserted into the patient's file.

Figure 16A:
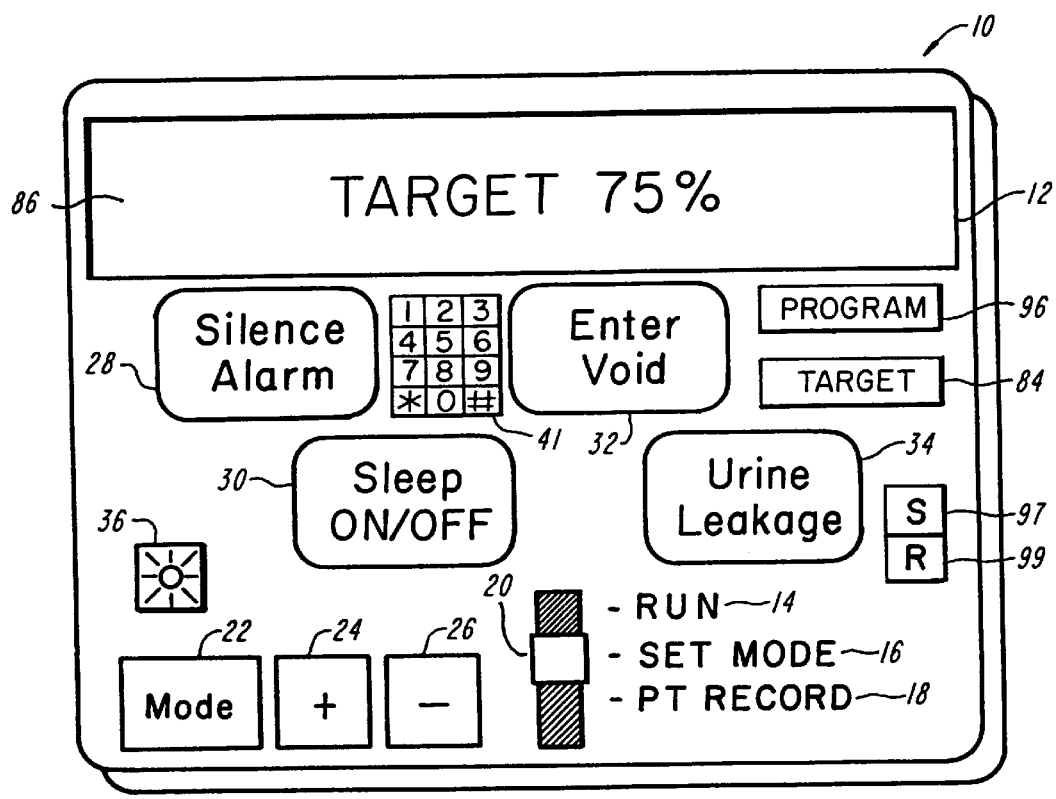
FIG. 16A illustrates an exterior of the device of the present invention displaying a target rate message.
Figure 16B:
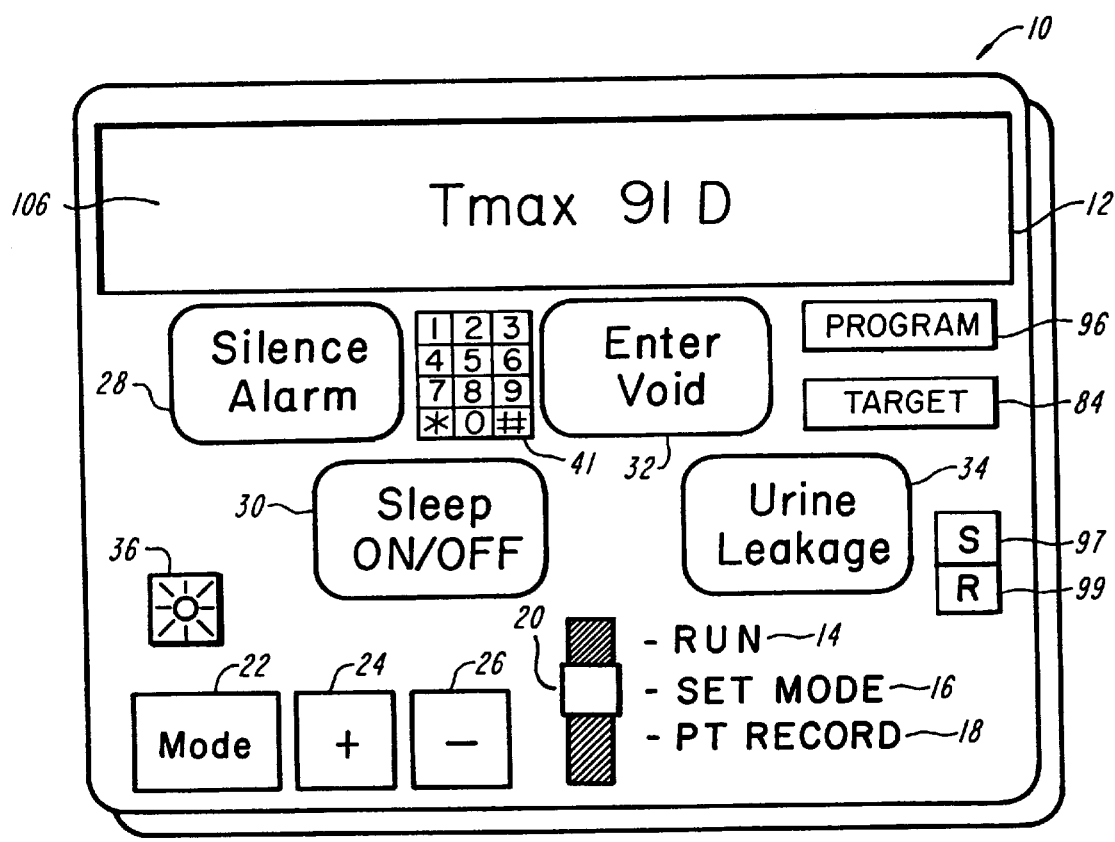
FIG. 16B illustrates an exterior of the device of the present invention displaying a message for the maximum number of days required to reach the target rate.

In still another embodiment, the device 10 can adjust the length of time between scheduled voidings ("SCHEDULED INTERVAL") based upon the patient's progress to date. The clinician can pre-program a target rate by pressing a "TARGET" button 84 while the switch 20 is in the "SET MODE" position 16, as shown in FIG. 16A. The LCD 12 can then display a "TARGET 75%" message 86 to show a default value for the target rate. The clinician can adjust this target value by pressing the "+" button 24 and the "−" button 26. When the clinician presses the target button 84 again, FIG. 16B illustrates that the LCD 12 can display a "Tmax 91D" message 106 to show a default value for the maximum number of days required to reach the target rate. The clinician can adjust this maximum target rate time period by pressing the "+" button 24 and the "−" button 26.

The target rate can be based on a variety of parameters such as, for example, a percentage of scheduled voidings relative to total number of scheduled and unscheduled voidings; an average inter-void interval rate ("AVERAGE IVI RATE"); and/or other parameters known by persons of ordinary skill in the art.

Figure 16C:
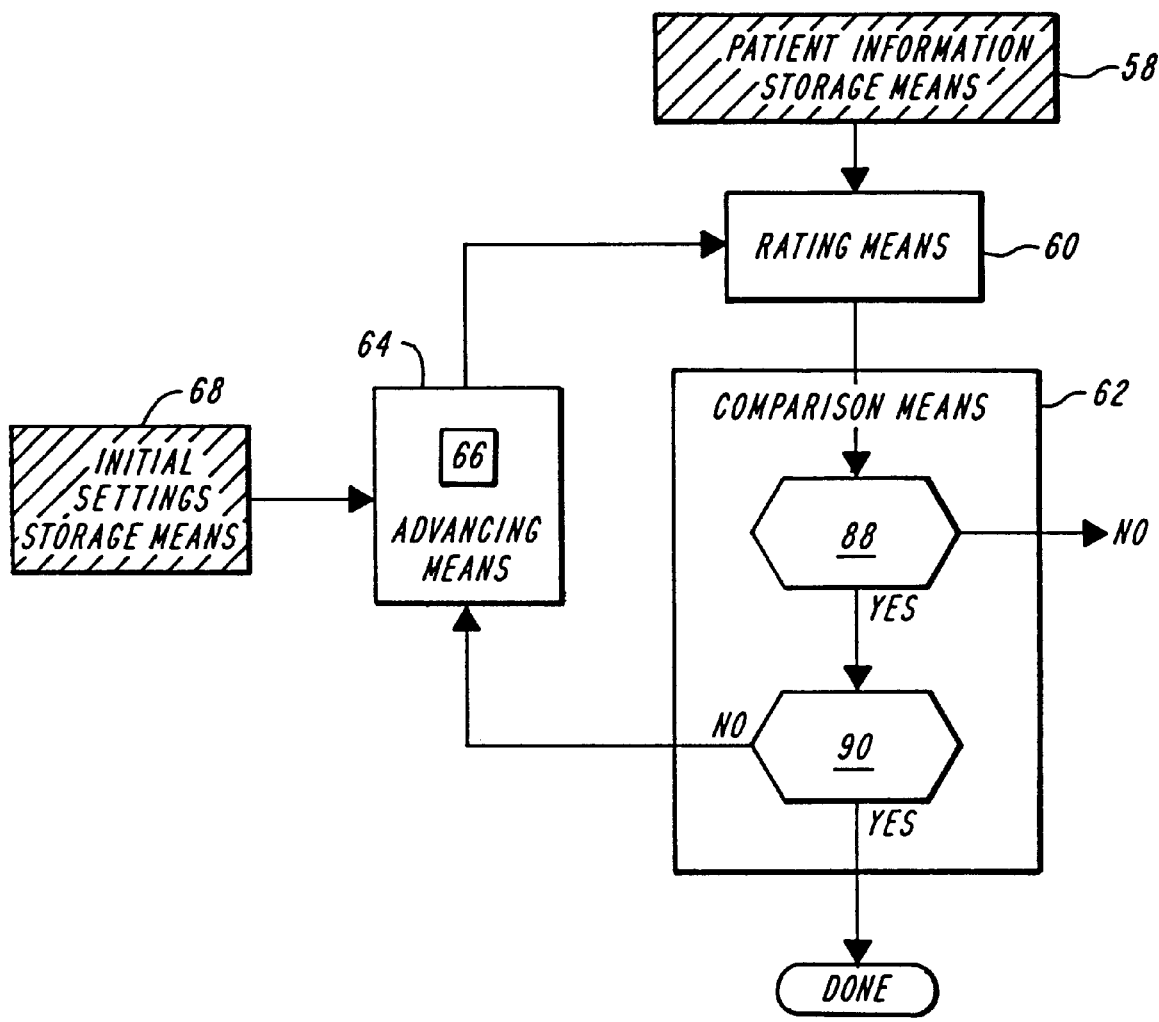
FIG. 16C is a flow chart of steps for storing initial intervals; calculating actual compliance rates; comparing actual compliance rates with pre-programmed target rates; and advancing pre-determined inter-void interval increments based upon the comparisons.

FIG. 16C shows a flow diagram of operations for storing initial settings; calculating actual compliance rates; comparing actual compliance rates with pre-programmed target rates; and advancing pre-determined voiding interval increments based upon the comparisons. Initial settings such as, for example, the scheduled inter-voiding intervals, scheduled inter-voiding interval increments, maximum inter-voiding intervals, and maximum number of days required to reach the target rate, can be stored in a pre-programmed settings storage element, as shown by box 68. Patient's entered information can be stored in a patient's information storage element, as shown by box 58.

The patient's entered information can be fed into a rating means 60 which can calculate a compliance rate based on a variety of parameters, such as, for example, the number of scheduled and unscheduled voidings and/or the average inter-void interval over a pre-determined period of time. The LCD 12 can display this calculated compliance rate.

At the end of a predetermined cycle, the actual compliance rate calculated in the rating means 60 can then be fed into a comparison means shown by box 62. Decision box 88 illustrates the comparison means 62 comparing the calculated compliance rate with the pre-programmed target rate. Control branches to "NO" and terminates further comparison, if the patient has not achieved the pre-programmed target rate. Control branches to "YES" and further branches to decision box 90, if the patient has achieved the pre-programmed target rate.

Decision box 90 illustrates the comparison means 62 comparing whether the patient has achieved, the maximum inter-voiding interval, the maximum target rate time period for attaining the target rate or otherwise completed the pre-determined patient protocol. Control branches to "DONE", where the patient has completed his or her bladder retraining, if the patient has competed the pre-determined patient protocol. Control branches to the advancing means 64, if the patient has not achieved the pre-determined patient protocol. The advancing means 64 can then adjust the "SCHEDULED INTERVAL" in the interval timer 66 according to the pre-programmed "INCREMENT".

Figure 17:
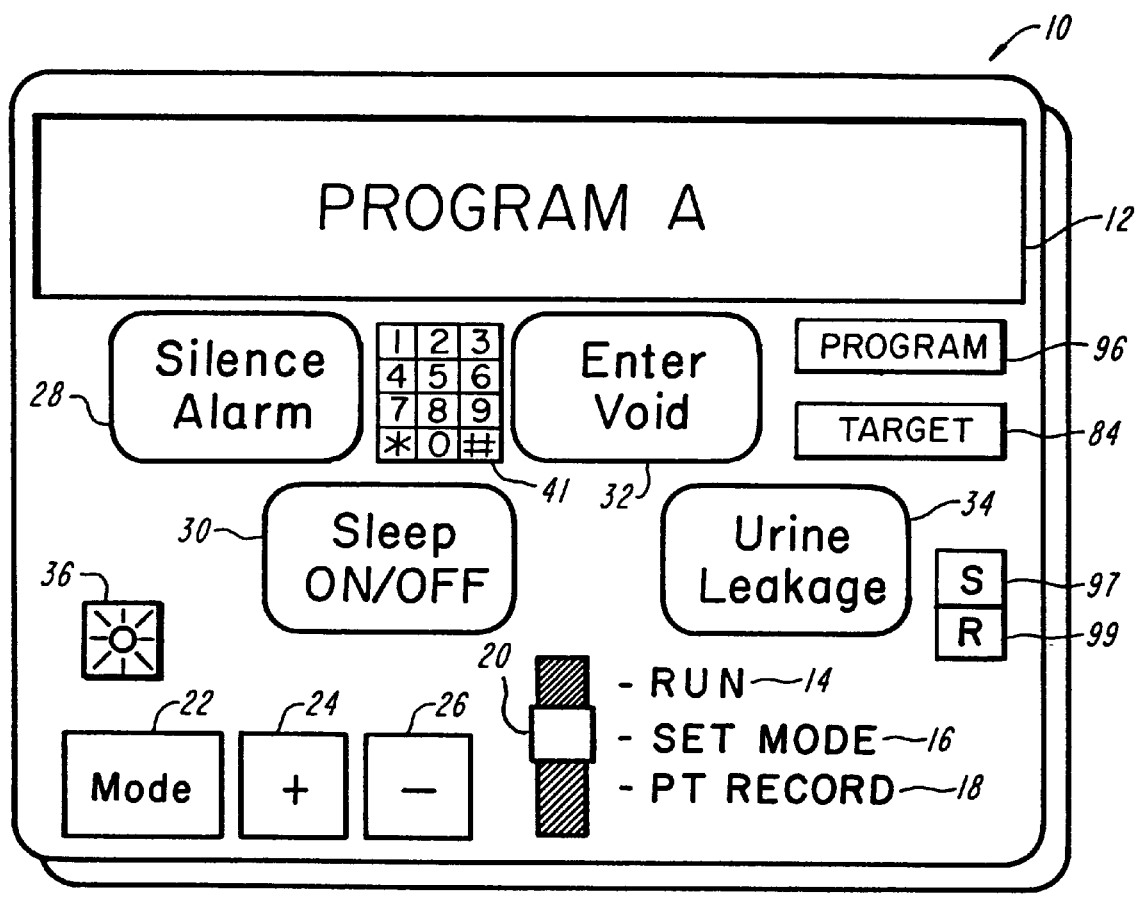
FIG. 17 illustrates the device of the present invention displaying a "PROGRAM A" message which indicates a pre-set treatment program.

In still another embodiment, FIG. 17 illustrates that the device 10 can be equipped with a program button 96 which can allow the clinician to program the device 10 with a number of preset treatment programs. The LCD 12 can display the program 98 chosen, i.e., Program A. The programs can be adjusted by pressing the "+" button 24 and the "−" button 26. Table I illustrates six preset treatment programs and one custom treatment program which can be used with device 10.

TABLE I

Preset Treatment Programs

| Program | Scheduled IVI[1] (hrs:min) | Increment (hrs:min) | Cycle (days) | Max Interval[2] (hrs:min) | Tmax[3] (days) |
|---|---|---|---|---|---|
| 1 | 1:00 | 0:15 | 7 | 3:00 | 91 |
| 2 | 1:00 | 0:30 | 7 | 3:00 | 70 |
| 3 | 1:30 | 0:15 | 4 | 3:00 | 77 |
| 4 | 2:00 | 0:15 | 4 | 3:00 | 63 |
| 5 | 0:30 | 0:15 | 14 | 3:00 | 110 |
| 6 | 2:00 | 0:00 | 7 | 2:00 | NA[4] |
| Custom | 0:14/4:00 | 0:00/1:00 | 3/14 | 0:15/4:00 | 1/110 |

[1]Scheduled Inter-void Interval can be based on the patient's voiding diary. This value can be an interval of time that the patients feel that they can comfortably wait between voids without feeling uncomfortable.
[2]Max Interval can be the maximum time between voids that the program will allow, and the program can continue at this interval indefinitely.
[3]Tmax can represent the number of days required for attaining the target rate, which is the maximum target rate time period.
[4]Not applicable.

Program 1 can be intended as the default preset treatment program, because it can represent the most commonly used treatment schedule.

Program 2 can be intended for patients who want to attempt bladder retraining at a faster pace.

Program 3 can be used for patients who feel they can comfortably begin bladder retraining at an interval of 1:30 between voids (which can be confirmed by a voiding diary).

Program 4 can be used for patients who do not complain of urinary frequency and can comfortably wait at least 2:00 between voids (which can be confirmed by a voiding diary).

Program 5 can be used for the unusual patient who has severe urinary frequency (with no evidence of lower urinary tract infection) and can rarely wait more than 0:30 between voids.

Program 6 can be used for the patient who would benefit from timed and/or prompted voiding and/or who is not receptive to bladder retraining.

Custom Program can be used to customize a program for a particular patient, selecting values for the parameters in the ranges indicated.

The clinician can select the appropriate starting program for the patient, and can change the program during treatment as function of the patient's progress. Alternatively, the device 10 initially can function primarily as a voiding diary, and subsequently can automatically select a starting program after a pre-determined period based upon, for example, the patient's average inter-voiding interval; and/or can change the program based upon a patient's progress to date as measured by, for example, a patient's average inter-voiding interval after a cycle period.

For example, Table II indicates which program the device 10 can automatically select based upon a patient's Average Inter-void Interval (AVG IVI).

TABLE II

Auto-program Selection

| AVG IVI (hrs:min) | Bladder Retraining Option (S: standard, R: rapid, and NA: Not Applicable) | Auto-program Selection |
|---|---|---|
| 1:00 ≤ AVG IVI < 1:30 | S | A |
| 1:00 ≤ AVG IVI < 1:30 | R | B |
| 1:30 ≤ AVG IVI < 2:00 | NA | C |
| 2:00 ≤ AVG IVI | NA | D |
| 0:30 ≤ AVG IVI < 1:00 | NA | E |

The device 10 can further provide options for different programs for patients who wish to attempt bladder retraining at a standard versus a more rapid bladder retraining rate. Accordingly, the clinician (and/or patient) can input the desired retraining option into the device to modify the device's automatic program selection function by pressing a "S" button 97 or a "R" button 99, as shown in FIG. 17.

These treatment programs are for exemplary purposes only, however. The programs can be modified by the clinician, both at the start of the treatment and during treatment. Not all patients, for example, will be able to reach the maximum interval between voidings. Other patients may find that the cycle length is too long (or too short), and the clinician may wish to modify this variable of a program during their treatment.

Figure 18:
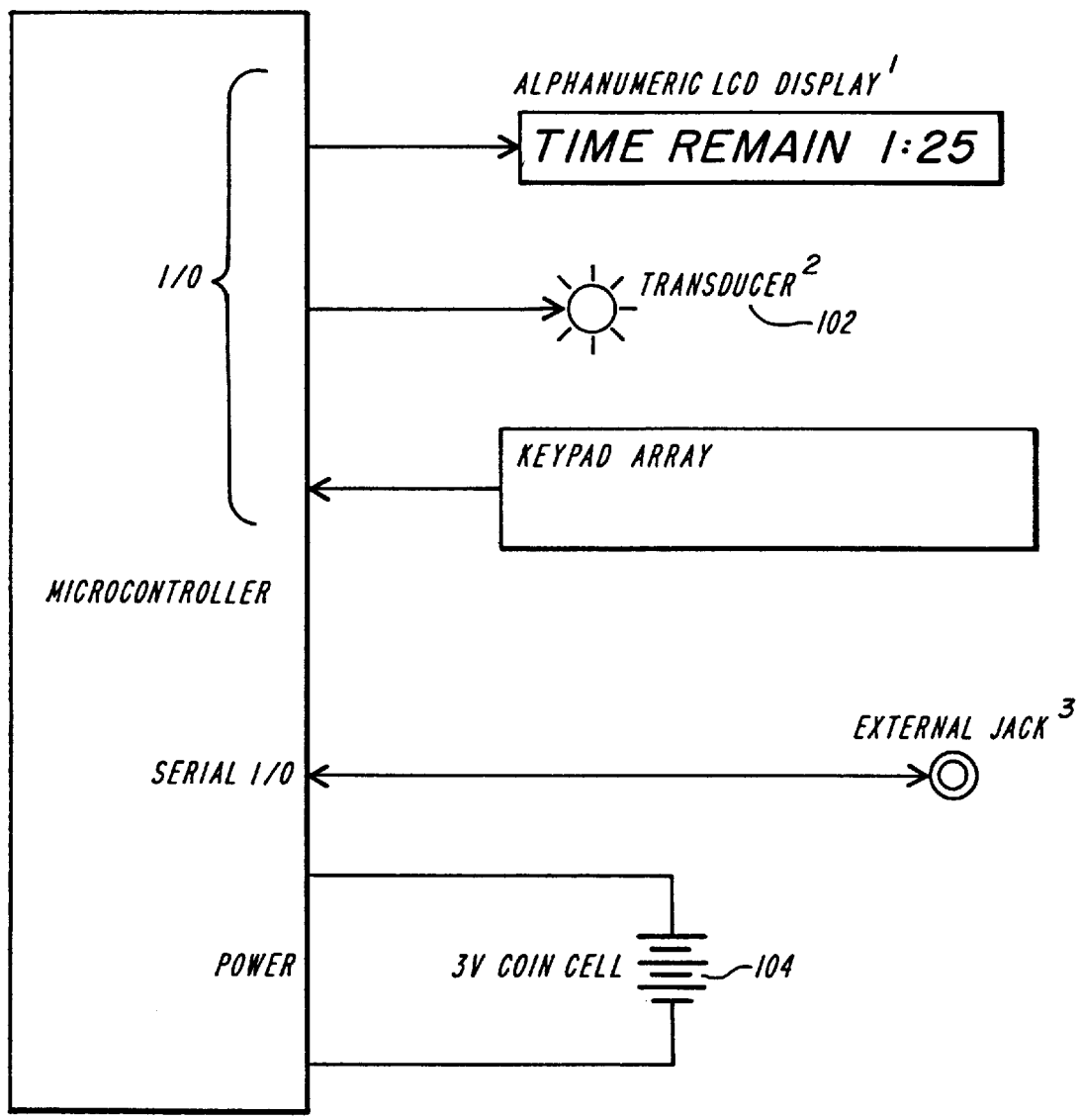
FIG. 18 illustrates a side view interior of the device of the present invention equipped with a transducer and a power cell.

FIG. 18 illustrates an interior side view of device 10 equipped with a transducer 102 and a power cell 104. Device 10 can be implemented, for example, with a microprocessor, such as Motorola Model 6805, manufactured by Motorola, Austin, Tex. The device 10 can also be equipped with a case, such as those available from Contour Plastics, Inc., Baldwin, Wis.; a LDC display, such as those available from Standish Industries, Lake Mills, Wis.; a LDC cover and switches such as those available from Miller Dial Corporation, El Monte, Calif.; a vibrating alarm, such as those available from Namiki Precision of America, Inc., Rochelle Park, N.J.; a buzzer, such as those available from Star Micronics America Inc, Piscataway, N.J.; printed circuit board materials, such as those available from Panasonic, Secaucus, N.J. and/or NEC Electronics, Mountain View, Calif.; and/or other peripheral electronic and and/or physical materials known to persons of ordinary skill in the art of the manufacture of portable electronic medical event reminder and monitoring devices.

Figure 19A:
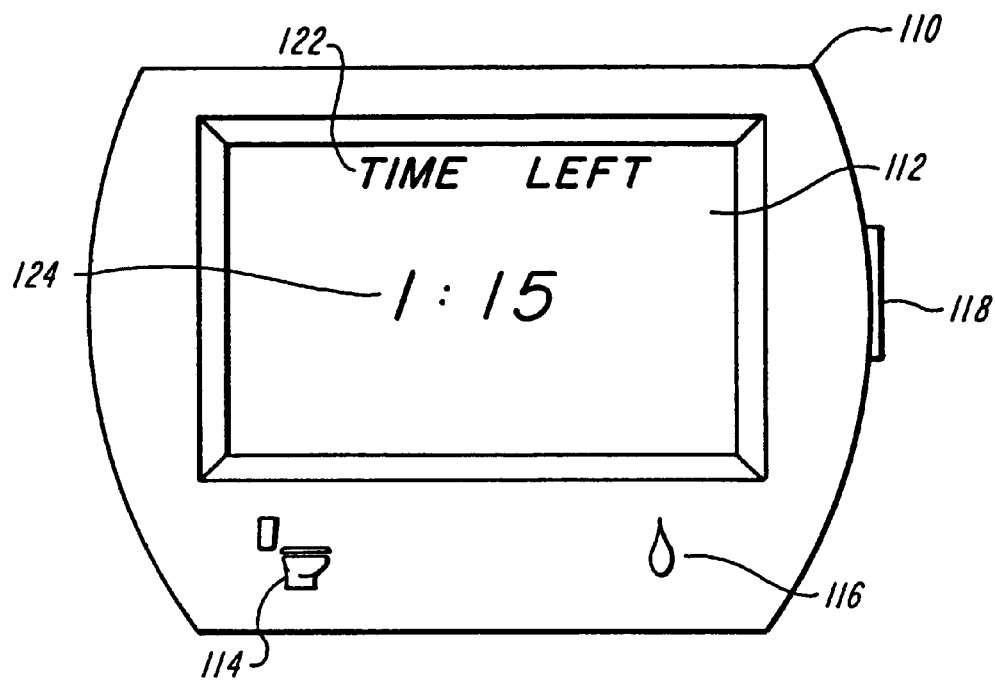
FIG. 19A illustrates another embodiment of the device of the present invention displaying a "TIME LEFT" message for instructing the patient as to the length of time remaining until the next scheduled medical event.

Various features of the device of the present invention such as, for example, the number, labeling, positioning and capabilities of buttons; and/or the ways the pre-determined settings and patient information are entered, confirmed and/or retrieved, can be varied based upon, inter alia, the programming configurations incorporated into the invention. For example, FIG. 19 illustrates another embodiment of a device 110 of the invention equipped with a display panel 112; a button 114 with a toilet symbol having an auto-repeat capability, for entering program and/or date, time and/or volume of scheduled voidings including voidings at and/or within a selected time period of the scheduled inter-void interval; a button 116 with a droplet symbol, also having an auto-repeat capability, for entering date, time and/or volume of unscheduled voidings, i.e., leak episodes; and a sleep button 118, also having auto-repeat capability, for putting the alarm in a stand-by state when the patient is sleeping at night and/or napping during the day. The display panel 112 can display a "TIME LEFT" message 122 to indicate the time remaining 124 (one hour and 15 minutes) until the next scheduled voiding.

Figure 19B:
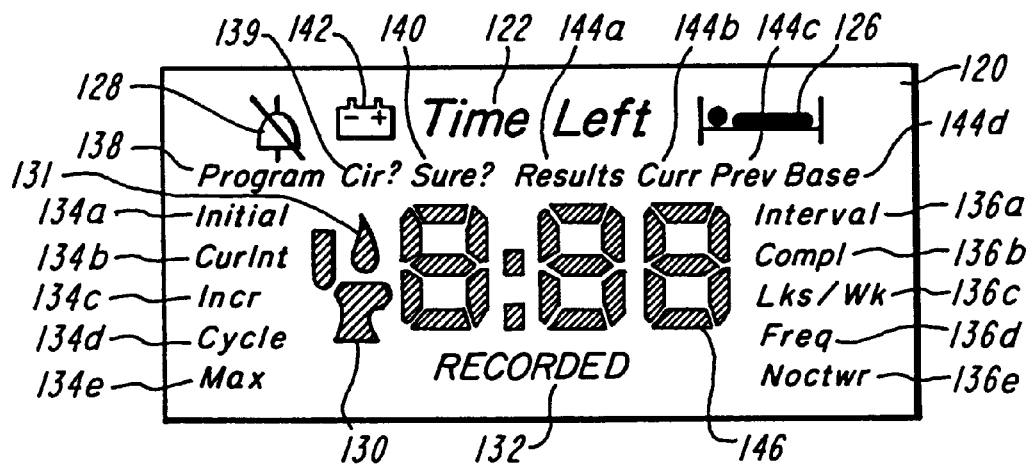
FIG. 19B illustrates an embodiment of the device of the present invention displaying showing an alternative display of information for the clinician and/or the patient.

FIG. 19B illustrates another embodiment of the device 110 of the invention showing an alternative display of information for the clinician and/or the patient. Typically, the clinician would access the more comprehensive display of information, however. The stand-by state of the device can be indicated by the bed symbol 126. Shut-off of the alarm can be indicated by the slashed bell symbol 128. The device 110 can display the toilet symbol 130 on the display panel 112 to confirm the recording of a scheduled (or near-scheduled) voiding episode. A droplet 131 can be displayed on the display panel 112 to confirm the recording of a non-scheduled leak episode. A "RECORDED" message 132 can also be displayed to confirm the recording of a scheduled or non-scheduled voiding episode.

In response to pressing various pre-determined sequences of the buttons 114, 116, and 118, the record of the pre-determined settings and the patient results can be displayed on the display panel 112, for example, in the space where the numbers 8:88, identified by element 146, are currently illustrated. Corresponding codes explaining the current display can be displayed. For example, the "Program" 138, "Initial" 134a, "Cur Int" 134b, "Incr" 134c, "Cycle" 134d, "Max" 134e, messages can be illuminated to the left of the values (not shown) for the pre-determined program, initial inter-void interval, current inter-void interval, increment (for augmenting the length of the inter-void interval), cycle time period to attain the pre-determined inter-void interval, and maximum inter-void interval and/or time period to attain the desired pre-determined inter-void interval, respectively.

The "Results" 144a and "Cur" 144b messages can be displayed while the "Interval" 136a, "Compl" 136b, "Lks/Wk" 136c, "Freq" 136d, "Noctur" 136e, messages are displayed to the right of values (not shown) for a patient's current inter-void interval setting, compliance rate, average leaks per week, average voiding frequency (including scheduled and unscheduled voids), and average nocturia, respectively, over the pre-determined cycle.

Similarly, the "Results" 144a and "Prev" 144b messages can be displayed while "Interval" 136a, "Compl" 136b, "Lks/Wk" 136c, "Freq" 136d, "Noctur" 136e, messages are displayed to the right of values (not shown) for a patient's previous inter-void interval setting, compliance rate, average leaks per week, average voiding frequency (including scheduled and unscheduled voids), and average nocturia, respectively, over a selected previous pre-determined cycle.

Further, the "Results" 144a and "Base" 144d messages can be displayed while "Interval" 136a, "Compl" 136b, "Lks/Wk" 136c, "Freq" 136d, "Noctur" 136e, messages are displayed to the right of values (not shown) for a patient's initial inter-void interval setting, compliance rate, average leaks per week, average voiding frequency (including scheduled and unscheduled voids), and average nocturia, respectively, over an initial pre-determined cycle.

The "Clr?" 139 message can be displayed during the clearing of programs, other settings, and/or the patient's results from the memory of the device 110. The "Sure" 140 message can be displayed as a confirmation message, confirming the entry of a patient's results, program and/or other settings, and/or as an additional message to confirm that clearing of programs, settings and/or results from memory is correct. The battery symbol 142 can be displayed when the battery is low.

In sum, the present invention benefits from the recognition that simple methods and devices which remind patients of scheduled medical events and allow patients to record both scheduled (including medical events at and/or within a selected time period of the scheduled intervals) and non-scheduled medical events assist the patients in medical event retraining and the clinician in accurately monitoring the patients' progress.

The devices and methods of the present invention have advantages over the traditional prompting and recording medical treatment techniques. The devices and methods of the present invention allow the patient to record both scheduled and non-scheduled medical events. The traditional techniques may not allow the patient to input an event which falls outside of the pre-determined schedule. In addition, the devices and methods of the present invention provide devices and methods which can adjust the pre-determined schedule for a medical event based upon a patient's progress to date in reaching a desired target. Traditional techniques may not adjust the pre-determined schedule based upon a patient's progress to date.

It will be understood that the above description is provided by way of illustration and not by way of limitation. For example, the number of buttons required to program and/or record information can be decreased and/or increased based upon the programming configurations incorporated into the invention. The invention is further characterized according to the following claims.

We claim:

1. A portable apparatus for prompting and recording a plurality of urination events, the apparatus comprising:

timing means for keeping time;

a scheduling means for storing a plurality of pre-determined time intervals;

a prompting means for issuing a prompting signal at at least one of the pre-determined time intervals;

a confirmation means for storing at least one scheduled controlled urination confirmation record when the prompting signal is issued;

an episode recording means for storing at least one non-scheduled uncontrolled urination episode record;

an accessing means for accessing the confirmation records and the non-scheduled episode records; and a rating means for determining a compliance rate based upon stored scheduled controlled urination confirmation records and non-scheduled uncontrolled urination episode records.

2. The apparatus of claim 1, further comprising:

a comparison means for comparing the compliance rate to a pre-determined target rate; and an advancing means for advancing the pre-determined time intervals to a plurality of advanced pre-determined time intervals when the compliance rate is at a minimum equal to the target rate.

3. The apparatus of claim 2, further comprising:

an advancing means for advancing the pre-determined time intervals to a plurality of advanced pre-determined time intervals when an option selection element is depressed.

4. The apparatus of claim 1, further comprising:

a communication means for downloading scheduled controlled urination confirmation records and non-scheduled uncontrolled urination episode records onto a personal computer.

5. The apparatus of claim 1, further comprising:

a printing means for printing scheduled controlled urination confirmation records and non-scheduled uncontrolled urination episode records onto a hard copy print-out.

6. The apparatus of claim 1, further comprising:

a display means for displaying at least one patient message.

7. The apparatus of claim 6 wherein the patient messages comprise:

a message for indicating the hours and minutes remaining until the next scheduled medical event;

a message for prompting a patient to turn off the prompting signal;

a message for prompting the patient to enter a scheduled controlled urination confirmation record;

a message for confirming that the patient has entered a scheduled controlled urination confirmation record; and a message for confirming that the patient has entered a non-scheduled uncontrolled urination episode record.

8. The apparatus of claim 1 wherein the prompting signal comprises a vibrating signal.

9. (New) The apparatus of claim 1, further comprising means for recording a volume of a scheduled controlled urination.

10. A portable apparatus for prompting and recording a plurality events, the apparatus comprising:

a timing means for keeping time;

a scheduling means for storing a plurality of pre-determined time intervals;

a prompting means for issuing a prompting signal at at least one of the pre-determined time intervals;

a confirmation means for storing at least one scheduled controlled urination confirmation record when the prompting signal is issued;

and episode recording means for storing at least one non-scheduled uncontrolled urination episode record;

a standby means for stopping the prompting means from issuing a prompting signal and for restarting the prompting means after a desired standby interval;

a display means for displaying a message prompting a patient that the apparatus is in a standby mode;

a standby interval recording means for at least one record of a length of time of the standby interval; and an accessing means for accessing the standby interval record.

11. A method for prompting and recording a plurality of urination events, the method comprising:

storing a plurality of pre-determined time intervals;

issuing a prompting signal at at lest one of the pre-determined time intervals;

storing at least one confirmation record about a scheduled controlled urination event when the prompting signal is issued;

storing at least one non-scheduled episode record about a non-scheduled urination event;

accessing the confirmation records and the non-scheduled episode records; and determined a compliance rate based upon the occurrence of scheduled controlled urination events and non-scheduled urination events.

12. The method of claim 11, further comprising the steps of:

comparing the compliance rate to a pre-determined target rate; and advancing the pre-determined time intervals to a plurality of advanced pre-determined time intervals when the compliance rate is at a minimum equal to the pre-determined target rate.

13. The method of claim 12, further comprising the steps of:

advancing the pre-determined time intervals to a plurality of advanced pre-determined time intervals when an option selection element is depressed.

14. The method of claim 12, further comprising the step of:

downloading the at least one confirmation record and the at least one non-scheduled episode record onto a personal computer.

15. The method of claim 12, further comprising the step of:

printing the at least one confirmation record and the at least one non-scheduled episode record onto a hard copy print-out.

16. The method of claim 12, further comprising the step of:

displaying at least one patient message.

17. The method of claim 16 wherein the step of displaying patient messages comprises:

indicating the hours and minutes remaining until the next scheduled controlled urination event;

prompting a patient to turn off the prompting signal;

prompting the patient to enter the at least one confirmation record;

confirming that the patient has entered the at least one confirmation record; and confirming that the patient has entered the at least one non-scheduled episode record.

18. The method of claim 12 wherein the step of issuing the prompting signal comprises issuing a vibrating prompting signal.

19. The method of claim 12, further comprising the step of recording a volume of a scheduled controlled urination.

20. A method for prompting and recording a plurality of urination events, the method comprising:

storing a plurality of pre-determined time intervals;

issuing a prompting signal at at least one of the pre-determined time intervals;

storing at least one confirmation record about a scheduled controlled urination event when the prompting signal is issued;

storing at least one non-scheduled episode record about a non-scheduled urination event;

accessing the confirmation records and the non-scheduled episode records;

stopping the prompting means from issuing a prompting signal;

display a message prompting a patient that the apparatus is in a standby mode;

restarting the prompting means after a desired standby interval;

storing at least one record of a length of time of the standby interval; and accessing the standby record.

* * * * *